United States Patent [19]

Uhlen

[11] Patent Number: 5,629,158

[45] Date of Patent: May 13, 1997

[54] SOLID PHASE DIAGNOSIS OF MEDICAL CONDITIONS

[75] Inventor: Mathias Uhlen, Uppsala, Sweden

[73] Assignee: CEMU Bitecknik AB, Uppsala, Sweden

[21] Appl. No.: 477,270

[22] Filed: Jun. 7, 1995

Related U.S. Application Data

[63] Continuation of Ser. No. 261,010, Jun. 14, 1994, abandoned, which is a continuation of Ser. No. 781,157, Nov. 7, 1991, abandoned.

[30] Foreign Application Priority Data

| Mar. 22, 1989 | [GB] | United Kingdom | 8906641 |
| Mar. 22, 1989 | [GB] | United Kingdom | 8906642 |

[51] Int. Cl.⁶ .............................. C12P 19/34; C12Q 1/68
[52] U.S. Cl. .............. 435/6; 435/91.2; 935/77; 935/78
[58] Field of Search .................. 435/6, 91.2; 935/77, 935/78

[56] References Cited

U.S. PATENT DOCUMENTS

| 4,777,129 | 10/1988 | Dattagupta et al. ............. 435/6 |
| 4,965,188 | 10/1990 | Mullis et al. ................. 435/6 |

FOREIGN PATENT DOCUMENTS

| 0198662 | 10/1986 | European Pat. Off. ............. 435/6 |
| WO90/063746 | 6/1990 | WIPO . |

OTHER PUBLICATIONS

Mullis et al., Cold Spring Harb. Symp. Quant. Biol. 51:263–273(1986).

Venetianer et al., PNAS, USA 71(10):3892–3895 (Oct. 1974).

Syvanen et al., Nuc. Acids Res. 16(23):11327–11338.

Kemp et al. (Apr. 1989) Proc. Nat'l Acad. Aci., U.S.A.86:2423 "Colorimetric detection of specific DNA polymerase chain reactions".

*Primary Examiner*—Stephanie W. Zitomer
*Attorney, Agent, or Firm*—Foley & Lardner

[57] ABSTRACT

A method of and kit for diagnosis of medical conditions by identification of specific DNA characterized in that DNA in a sample is subjected to initial amplification by the polymerase chain reaction (PCR) method using a first pair of primers specific to the target DNA and the amplified DNA so produced is further amplified by the PCR method using a second primer pair, one or both of which are different from either of said first primer pair and are specific to a sequence or sequences of the target DNA between the hybridization sites of said first primer pair, one of the primers of said second primer pair being immobilized on a solid support or being provided with means for subsequent attachment to a solid support and the other of said second pair of primers carrying a label or being provided with means for subsequent attachment to a label, said amplification being followed by separation of said solid support carrying said amplified DNA and detection of label attached thereto, one or both of said means for subsequent attachment comprising a distal DNA sequence carried by the said primer which does not hybridize with the target DNA but has a selective affinity for a binding partner attached to either a solid support or a label.

21 Claims, 16 Drawing Sheets

STREPTOCOCCAL PROTEIN G GENE

STAPHYLOCOCCAL PROTEIN A GENE

FIG. 16

| | | | |
|---|---|---|---|
| RIT33 | P falciparum | +1377 | FLANKING PRIMER | 5'-CCTCCTGATATTGATCATAC-3' |
| RIT34 | " | +1804 | " | 5'-AATATTTCTGCCTGTACCAG-3' |
| RIT35 | " | +1421 | INNER PRIMER | 5'-CCATGATTACGAATTAATACGAATTCGTTCATGACTGATGTAAATA-3' |
| RIT36 | " | +1761 | " | 5'-AATTGTTATCCGCTCACAATTAAGCTTCTTTCTTCAAGTTCTCTCC-3' |

| | | |
|---|---|---|
| RIT6 | lacOP | GENERAL BIOTINYLATED PRIMER | 5'-biotin-CCATGATTACGAATTAATAC-3' |
| RIT43 | | GENERAL FLOURESCENT PRIMER | 5'-FITC-AATTGTTATCCGCTCACAATT-3' |

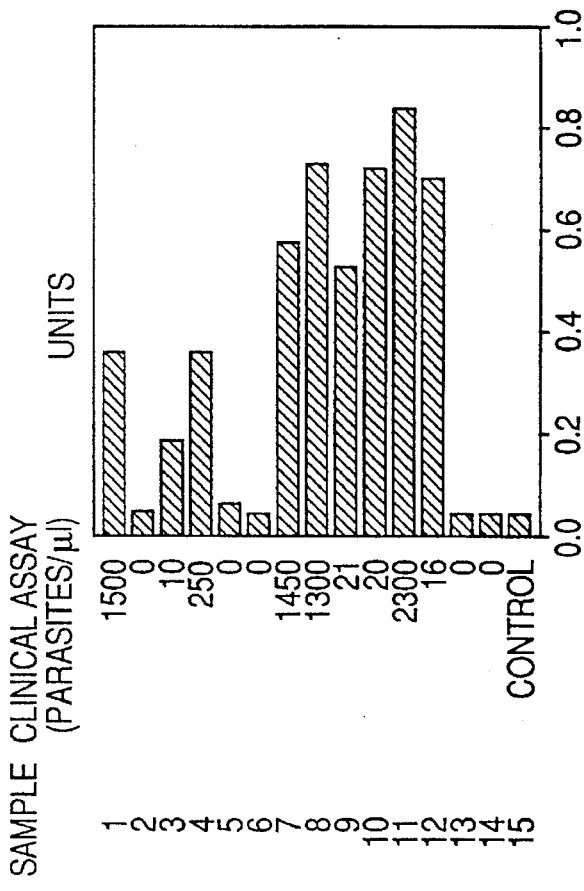

FIG. 17

FIG. 18
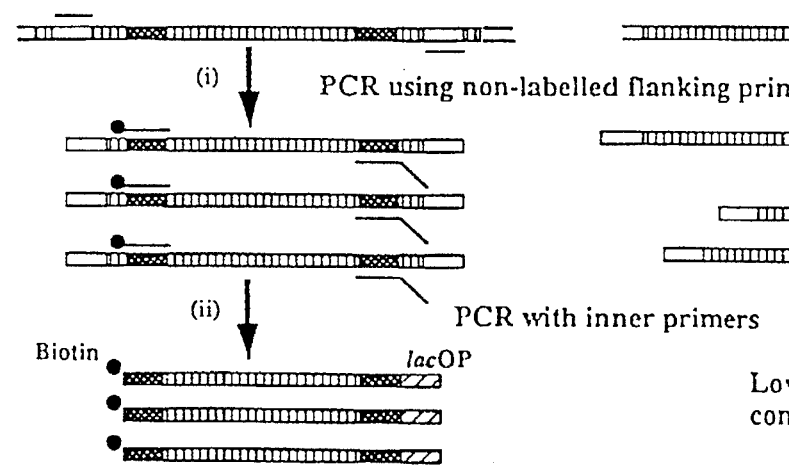
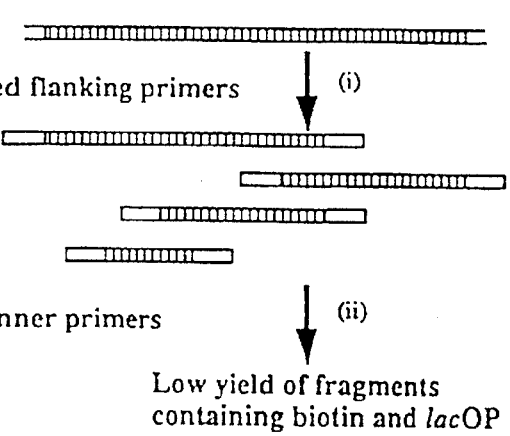
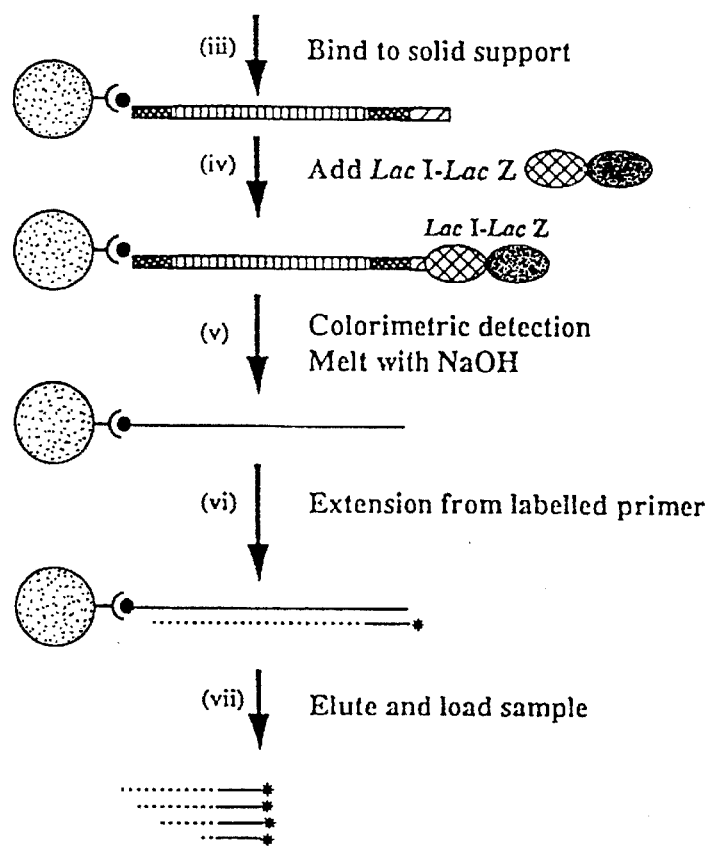

FIG. 19

```
                RIT 23                    Biotin           RIT 25
1013 GCA ATG GTT TCT TAC TGT GGA GGA CAT AAA AAT ACA GCA AGG GTA ACA
 265 Ala Met Val Ser Tyr Cys Gly Gly His Lys Asn Thr Ala Ser Val Thr
                             T
1062 ACT GTG ATC AAC GAG CCT TGC GTA CAA GTA AGT ATT GCA GGA GCA GAT
 281 Thr Val Ile Asn Glu Pro Cys Val Gln Val Ser Ile Ala Gly Ala Asp 1108 TGG TCT TAT GTT TGT AAG CCT GTA GAA TAT GTG ATC TCC GTT TCC AAT
 297 Trp Ser Tyr Val Cys Lys Pro Val Glu Tyr Val Ile Ser Val Ser Asn
                                                G
1157 CGT GGA GAT CTT GTG TTG CGA GAT GTC GTC AAA GAC ACT CTT TGT AAT
 313 Pro Gly Asp Leu Val Leu Arg Asp Val Val Lys Asp Thr Leu Ser
                                                Glu 1205 CCC GGA GTC ACA GTT CTT GAA GCT GCA GGA GCT CAA ATT TCT TGT AAT
 329 Pro Gly Val Thr Val Leu Glu Ala Ala Gly Ala Gln Ile Ser Cys Asn
                                 RIT 26                 Lac op
1253 AAA GTT TGG ACT GTG AAA GAA CTG AAT CCT GGA GAG TCT CTA CAG
 345 Lys Val Trp Thr Val Lys Glu Leu Asn Pro Gly Glu Ser Leu Gln
                              RIT 24
1301 TAT AAA GTT CTA GTA AGA GCA CAA ACT CCT GGA CAA TTC
 361 Tyr Lys Val Leu Val Arg Ala Gln Thr Pro Gly Gln Phe
```

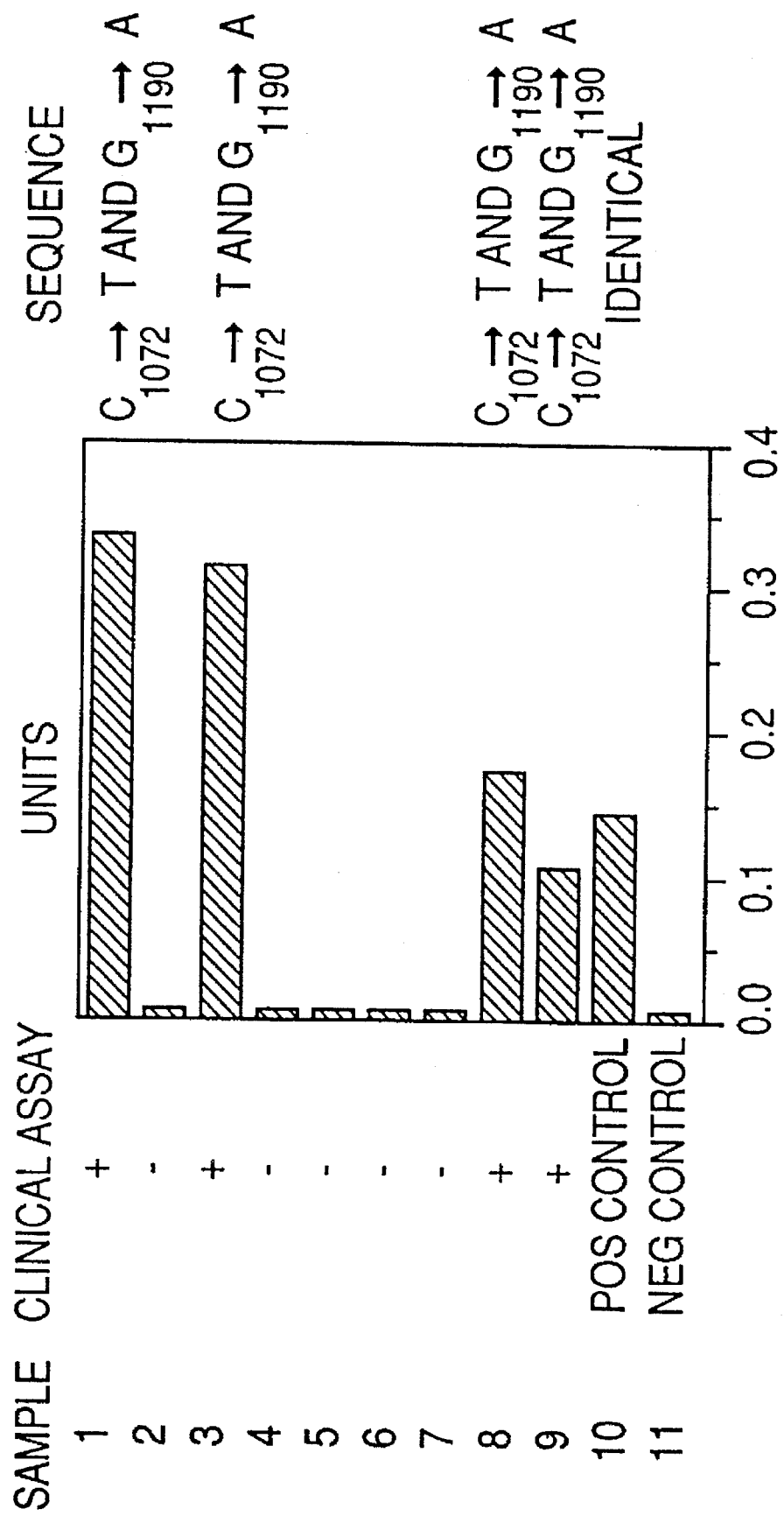

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i ) ORIGINAL SOURCE:
        ( B ) STRAIN: RIT 1

( x i ) SEQUENCE DESCRIPTION: SEQ ID NO:1:

AATAGCGTGA TTTTGCGGT ( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 2

( x i ) SEQUENCE DESCRIPTION: SEQ ID NO:2:

GACCACCGCA TTGTGGACGT GACCGGCAGC AAAATG      36

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 3

( x i ) SEQUENCE DESCRIPTION: SEQ ID NO:3:

CTATATATTT TATCTGTTTT TATT      24

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 4

( x i ) SEQUENCE DESCRIPTION: SEQ ID NO:4:

CGTTTACGAC GCGTTGTGC      19

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 5

( x i ) SEQUENCE DESCRIPTION: SEQ ID NO:5:

CCATGATTAC GAATTTAATA CAATAGCGTG ATTTTGCGGT      40

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( v i i ) IMMEDIATE SOURCE:
    ( B ) CLONE: RIT 6

( x i ) SEQUENCE DESCRIPTION: SEQ ID NO:6:

CCATGATTAC GAATTTAATA C                                      21

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 7

( x i ) SEQUENCE DESCRIPTION: SEQ ID NO:7:

TGACCGGCAG CAAAATG                                           17

( 2 ) INFORMATION FOR SEQ ID NO:8:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 8

( x i ) SEQUENCE DESCRIPTION: SEQ ID NO:8:

CGGATCCATG GCAGGCCTTG CATTACCTAA GACTGACA                    38

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 9

( x i ) SEQUENCE DESCRIPTION: SEQ ID NO:9:

AATGCCATTG ACTTTACCAA TGCTTAAGG                              29

( 2 ) INFORMATION FOR SEQ ID NO:10:

( i ) SEQUENCE CHARACTERISTICS:
        ( A ) LENGTH: 49 base pairs
        ( B ) TYPE: nucleic acid
        ( C ) STRANDEDNESS: single ( D ) TOPOLOGY: linear ( i i ) MOLECULE TYPE: Other nucleic acid;
    ( A ) DESCRIPTION: Synthetic DNA oligonucleotide ( v i i ) IMMEDIATE SOURCE:
    ( B ) CLONE: RIT 10

( x i ) SEQUENCE DESCRIPTION: SEQ ID NO:10:

```
CCATGATTAC  GAATTAATA  CGTCGACATG  GAATTAACAC  CAGCCGTGA                49
```

( 2 ) INFORMATION FOR SEQ ID NO:11:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( v i i ) IMMEDIATE SOURCE:
    ( A ) LIBRARY: RIT 11

( x i ) SEQUENCE DESCRIPTION: SEQ ID NO:11:

```
TCAATGACTT  TTTGGTCTTT  ACTCCTAGGT  TAACACTCGC  CTATTGTTAA              50
```

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( v i i ) IMMEDIATE SOURCE:
    ( B ) CLONE: RIT 12

( x i ) SEQUENCE DESCRIPTION: SEQ ID NO:12:

```
GACCACCGCA  TTGTGGACGT  TAACACTCGC  CTATTGTTAA                          40
```

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( i v ) ANTI-SENSE: YES ( x i ) SEQUENCE DESCRIPTION: SEQ ID NO:13:

```
AATTGTTATC  CGCTCACAAT  T                                               21
```

( 2 ) INFORMATION FOR SEQ ID NO:14:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide (x i) SEQUENCE DESCRIPTION: SEQ ID NO:14:

ATTCCCGGGA TCCTCTGCCC GCTTTCCAG                                              29

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (i i) MOLECULE TYPE: Other nucleic acid;
        (A) DESCRIPTION: Synthetic DNA oligonucleotide (i x) FEATURE:
        (A) NAME/KEY: CDS
        (B) LOCATION: 1..21

(x i) SEQUENCE DESCRIPTION: SEQ ID NO:15:

CGA CTG GAA AGC GGG CAG TGAGCGCAAC GCAATTAATG TGAGTTAGGA                     48
Arg Leu Glu Ser Gly Gln
 1               5

TCCCCGGGAA TT                                                                60

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (i i) MOLECULE TYPE: protein (x i) SEQUENCE DESCRIPTION: SEQ ID NO:16:

Arg Leu Glu Ser Gly Gln
 1               5

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (i i) MOLECULE TYPE: Other nucleic acid;
        (A) DESCRIPTION: Synthetic DNA oligonucleotide (i x) FEATURE:
        (A) NAME/KEY: CDS
        (B) LOCATION: 1..33

(x i) SEQUENCE DESCRIPTION: SEQ ID NO:17:

CGA CTG GAA AGC GGG CAG AGG ATC CCC GGG AAT                                  33
Arg Leu Glu Ser Gly Gln Arg Ile Pro Gly Asn
 1               5                   10

(2) INFORMATION FOR SEQ ID NO:18:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:18:

Arg Leu Glu Ser Gly Gln Arg Ile Pro Gly Asn
 1               5                   10

(2) INFORMATION FOR SEQ ID NO:19:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii i) MOLECULE TYPE: Other nucleic acid;
        (A) DESCRIPTION: Synthetic DNA oligonucleotide (ix) FEATURE:
        (A) NAME/KEY: CDS
        (B) LOCATION: 1..327

(ix) FEATURE:
        (A) NAME/KEY: misc_difference
        (B) LOCATION: replace(60, "")
        (D) OTHER INFORMATION: /note="The C at positon 60 can
        also be a T. The amino acid at position 20 will
        be Asn in either case."

(ix) FEATURE:
        (A) NAME/KEY: misc_difference
        (B) LOCATION: replace(178, "")
        (D) OTHER INFORMATION: /note="The A at positon 178 can
        also be a G. If it is a G, then the amino acid at
        position 60 Glu instead of Lys."

(xi) SEQUENCE DESCRIPTION: SEQ ID NO:19:

```
GCA  ATG  GTT  TCT  TAC  TGT  GGA  GGA  CAT  AAA  AAT  ACA  GCA  AGG  GTA  ACA      48
Ala  Met  Val  Ser  Tyr  Cys  Gly  Gly  His  Lys  Asn  Thr  Ala  Arg  Val  Thr
 1              5                        10                       15

ACT  GTG  ATC  AAC  GAG  CCT  TGC  GTA  CAA  GTA  AGT  ATT  GCA  GGA  GCA  GAT      96
Thr  Val  Ile  Asn  Glu  Pro  Cys  Val  Gln  Val  Ser  Ile  Ala  Gly  Ala  Asp
                 20                       25                       30

TGG  TCT  TAT  GTT  TGT  AAG  CCT  GTA  GAA  TAT  GTG  ATC  TCC  GTT  TCC  AAT     144
Trp  Ser  Tyr  Val  Cys  Lys  Pro  Val  Glu  Tyr  Val  Ile  Ser  Val  Ser  Asn
             35                       40                       45

CGT  GGA  GAT  CTT  GTG  TTG  CGA  GAT  GTC  GTC  GTT  AAA  GAC  ACT  CTT  TCT     192
Arg  Gly  Asp  Leu  Val  Leu  Arg  Asp  Val  Val  Val  Lys  Asp  Thr  Leu  Ser
         50                       55                       60

CCC  GGA  GTC  ACA  GTT  CTT  GAA  GCT  GCA  GGA  GCT  CAA  ATT  TCT  TGT  AAT     240
Pro  Gly  Val  Thr  Val  Leu  Glu  Ala  Ala  Gly  Ala  Gln  Ile  Ser  Cys  Asn
 65                       70                       75                       80

AAA  GTA  GTT  TGG  ACT  GTG  AAA  GAA  CTG  AAT  CCT  GGA  GAG  TCT  CTA  CAG     288
Lys  Val  Val  Trp  Thr  Val  Lys  Glu  Leu  Asn  Pro  Gly  Glu  Ser  Leu  Gln
                     85                       90                       95

TAT  AAA  GTT  CTA  GTA  AGA  GCA  CAA  ACT  CCT  GGA  CAA  TTC                     327
Tyr  Lys  Val  Leu  Val  Arg  Ala  Gln  Thr  Pro  Gly  Gln  Phe
              100                      105
```

(2) INFORMATION FOR SEQ ID NO:20:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:20:

```
Ala  Met  Val  Ser  Tyr  Cys  Gly  Gly  His  Lys  Asn  Thr  Ala  Arg  Val  Thr
 1              5                        10                       15

Thr  Val  Ile  Asn  Glu  Pro  Cys  Val  Gln  Val  Ser  Ile  Ala  Gly  Ala  Asp
                 20                       25                       30

Trp  Ser  Tyr  Val  Cys  Lys  Pro  Val  Glu  Tyr  Val  Ile  Ser  Val  Ser  Asn
             35                       40                       45
```

| | | | | | | | | | | | | | |
|---|---|---|---|---|---|---|---|---|---|---|---|---|---|
|Arg|Gly|Asp|Leu|Val|Leu|Arg|Asp|Val|Val|Lys|Asp|Thr|Leu Ser|
| |50| | | |55| | | |60| | | | |
|Pro|Gly|Val|Thr|Val|Leu|Glu|Ala|Ala|Gly|Ala|Gln|Ile|Ser Cys Asn|
|65| | | |70| | | |75| | | | |80|
|Lys|Val|Val|Trp|Thr|Val|Lys|Glu|Leu|Asn|Pro|Gly|Glu|Ser Leu Gln|
| | | |85| | | |90| | | | |95| |
|Tyr|Lys|Val|Leu|Val|Arg|Ala|Gln|Thr|Pro|Gly|Gln|Phe| |
| | | |100| | | |105| | | | | | |

( 2 ) INFORMATION FOR SEQ ID NO:21:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:21:

GAGCTCCTGC AGCTTCAAGA ACTGTGACTC CGGGAGAAAG AGTGTCTTCA ACGACGACAT     60

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 23

( x i ) SEQUENCE DESCRIPTION: SEQ ID NO:22:

GCAATGGTTT CTTACTGTGG A     21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 24

( x i ) SEQUENCE DESCRIPTION: SEQ ID NO:23:

CTAGTAAGAG CACAAACTCC T     21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:

(B) CLONE: RIT 25

(x i) SEQUENCE DESCRIPTION: SEQ ID NO:24:

GGACATAAAA ATACAGCAAG G                                                      21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (v i i) IMMEDIATE SOURCE:
        (B) CLONE: RIT 26

(x i) SEQUENCE DESCRIPTION: SEQ ID NO:25:

GTAGTTTGGA CTGTGAAAGA A                                                      21

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (v i i) IMMEDIATE SOURCE:
        (B) CLONE: RIT 33

(x i) SEQUENCE DESCRIPTION: SEQ ID NO:26:

CCTCCTGATA TTGATCATAC                                                        20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (v i i) IMMEDIATE SOURCE:
        (B) CLONE: RIT 34

(x i) SEQUENCE DESCRIPTION: SEQ ID NO:27:

AATATTTCTG CCTGTACCAG                                                        20

(2) INFORMATION FOR SEQ ID NO:28:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (v i i) IMMEDIATE SOURCE:
        (B) CLONE: RIT 35

(x i) SEQUENCE DESCRIPTION: SEQ ID NO:28:

```
CCATGATTAC GAATTTAATA CGAATTCTGT TCATGACTGA TGTAAATA                                              4 8
```

( 2 ) INFORMATION FOR SEQ ID NO:29:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 36

( x i ) SEQUENCE DESCRIPTION: SEQ ID NO:29:

```
AATTGTTATC CGCTCACAAT TAAGCTTCTT TCTTCAAGGT TCTCTCC                                               4 7
```

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( v i i ) IMMEDIATE SOURCE:
        ( B ) CLONE: RIT 43

( x i ) SEQUENCE DESCRIPTION: SEQ ID NO:30:

```
AATTGTTATC CGCTCACAAT T                                                                          2 1
```

SOLID PHASE DIAGNOSIS OF MEDICAL CONDITIONS

This application is a continuation of application Ser. No. 08/261,010, filed Jun. 14, 1994, now abandoned, which is a continuation of Ser. No. 07/781,157, filed on Nov. 7, 1991, now abandoned.

This invention relates to a solid phase diagnosis of medical conditions by the identification of specific DNA.

Target DNA molecules are often present in cell lysates or other source materials in extremely small quantities and in order to amplify such DNA selectively, the polymer chain reaction (PCR) method has been developed. In this technique a pair of polymerisation primers specific to known sequences of the target DNA are selected, one hybridising at or near the 5' end of the coding strand and the other at or near the 5' end of the non-coding strand such that in the presence of a polymerase, each primer produces a DNA sequence extending the full length of the target DNA template. If the DNA so produced is then subjected to strand separation, typically by melting at a temperature of about 90° C., the newly formed single stranded DNA sequences will hybridise to excess primer present in the mixture, usually after reducing the temperature to the range suitable for annealing, whereupon in the presence of the polymerase, further DNA strands are synthesised, this time extending only between the termini of the two primers. The polymerase is preferably capable of surviving the high temperature used in the strand separation step, a suitable thermophilic polymerase, namely Taq, having recently become available. If an excess of the two primers and of nucleotides needed for DNA synthesis is maintained in the medium, it is possible to operate a repeated cyclic process in which the separate strands are synthesised, separated, annealed to primer and new strands synthesised, merely by raising and lowering the temperature between the optimal temperatures for each of the above stages. In this way, it is found that amplification of the original target DNA can be exponential and million-fold increases of concentration can be effected in a relatively short time.

However, this procedure is not always sufficiently selective due to a percentage of non-specific binding of the primers to other DNA sequences, thereby amplifying the latter in addition to the target DNA. This amplification of random portions of sample DNA, due to the non-specific binding of the primers, leads to an increase in background noise relative to the signal from the target DNA. My experiments show that in many cases this increase in the level of background noise can severely affect the usefulness of this technique.

In relation to molecular cloning, it has been suggested that this problem of non-specific binding of the primers may be overcome by using a second pair of primers nested within the first. By requiring four separate priming events to take place considerable reduction in non-specific amplification is achieved (see Mullis, K. B. K. Faloona, F. A., Methods in Enzymology (1987) 155 pp 335–350, Wrischnik, L. A. et al. Nuc. Acids Res. (1987) 15 pp 529–542) and U.S. Pat. Nos. 4,683,195 and 4,683,202. Engelke, D. R. et al (Proc. Natl. Acad. Sci U.S.A. (1988) 85 pp 544–548) suggests that only one new primer, nested inside one or other of the original primers, can lead to a larger and more consistent amplification of the target DNA. The above work by Mullis, Faloona and others was primarily concerned with molecular cloning and sequence analysis. Some workers in this field realised that the amplified DNA would have termini corresponding to the primers and that the primers could incorporate one or more restriction sites which are not present in the target DNA. Once amplification had taken place, the termini of the amplified DNA could be cut with the appropriate restriction enzyme or enzymes to give sticky ends. The sticky ends could then be used for the incorporation of the target DNA into an appropriate vector for cloning.

Detection of amplified target DNA has been disclosed by Mullis, K. B. et al in U.S. Pat. No. 4,683,195. A labelled probe is used to detect the amplified DNA via the conventional southern blotting technique. Although this is a very sensitive and powerful technique, it is very time consuming (especially if radiolabels are used) requiring a great deal of skill and is itself subject to non-specific interactions leading to background noise.

Other methods of diagnosing medical conditions by the identification of specific DNA have included those based on DNA polymorphism. The two main techniques based on DNA polymorphism are restriction fragment length polymorphism "RFLP" and mini-satellite polymorphism. Both these techniques can be used in conjunction with PCR. Both depend on enzymic digestion of target DNA in combination with electrophoresis and use of a labelled probe or probes to give so-called "genetic fingerprints" which need to be read by an expert skilled in electrophoretic techniques, especially if any comparisons with other electrophoretic gels are necessary.

None of the prior art has provided a simple and rapid method of diagnosis of medical conditions by identification of specific DNA which method is free from the disadvantages of non-specific binding present in both the usual PCR technique and methods involving electrophoretic gels.

We have found that by combining the two-stage PCR amplification technique with solid phase isolation of the amplified target DNA it is possible to identify target DNA even at very low initial concentrations with significantly reduced background noise and hence greater accuracy than previous diagnostic methods, while avoiding time-consuming detection steps such as Southern blotting.

Y. M. D. Lo et al (Nucleic Acids Research, 16, 8719, 1988) have described carrying out PCR using biotinylated dUTP to provide amplified target DNA labelled with biotin. There is no suggestion of using the biotinyl groups for immobilisation and in this method all the U bases carry biotin groups rather than there being only terminal biotin groups.

European Patent Application 192168 of Molecular Diagnostics describes the use of dual probes for hybridization to target DNA to provide added selectively, one probe carrying means for immobilisation and the other carrying detection means. However, there is no suggestion of using such probes as primers in PCR amplification.

However, in such a system, it is generally the case that the primer(s) permitting immobilization to a solid support or labelling comprise a DNA sequence specific to the target DNA coupled to a non DNA grouping which has to be attached separately by chemical means.

The present invention provides, inter alia, a method whereby primer used in the final PCR amplification stage can comprise a non-DNA moiety joined to a standard or general DNA sequence which can be used in the amplification of any target DNA. This is achieved by constructing at least one of the second stage PCR primers with a 'handle' comprising a DNA sequence not hybridising to the target DNA, this handle being specific to a general DNA sequence attached to an inert support or a label so that the latter can be used in a variety of assays and does not need to be synthesised specially for a particular target DNA sequence.

Although the primer(s) having a handle require synthesis to correspond to any particular target DNA, this can be completed on a standard DNA synthesis system without the need to use additional chemical methods for attaching the inert support label. It is particularly useful to be able to use radioisotopes pre-attached to a standard binding ligand or probe and thus to avoid the need for local chemical manipulation of radioactive materials.

This technique may conveniently be termed detection of immobilised amplified nucleic acids (DIANA).

According to the present invention there is provided a method of diagnosis of medical conditions by identification of specific DNA characterized in that DNA in a sample is subjected to initial amplification by the polymerase chain reaction (PCR) method using a first pair of primers specific to the target DNA and the amplified DNA so produced is further amplified by the PCR method using a second primer pair, one or both of which are different from either of said first primer pair and are specific to a sequence or sequences of the target DNA between the hybridization sites of said first primer pair, one of the primers of said second primer pair being immobilised on a solid support or being provided with means for subsequent attachment to a solid support and the other of said second pair of primers carrying a label or being provided with means for subsequent attachment to a label, said amplification being followed by separation of said solid support carrying said amplified DNA and detection of label attached thereto, one or both of said means for subsequent attachment comprising a distal DNA sequence carried by the said primer which does not hybridise with the target DNA but has a selective affinity for a binding partner attached to either a solid support or a label.

Any suitable polymerase may be used, although it is preferred to use a thermophilic enzyme such as Taq polymerase to permit the above repeated temperature cycle without having to add further polymerase, e.g. Klenow fragment, in each cycle.

It should be noted that the target DNA may be cDNA synthesised from mRNA in the sample and the method of the invention is thus applicable to diagnosis on the basis of characteristic mRNA. Such preliminary synthesis can be carried out by a preliminary treatment with a reverse transcriptase, conveniently in the same system of buffers and bases to be used in the subsequent PCR steps. Since the PCR procedure requires heating to effect strand separation, the reverse transcriptase will be inactivated in the first PCR cycle. When mRNA is the target nucleic acid, it may be advantageous to submit the initial sample, e.g. a serum sample, to treatment with an immobilised polydT oligonucleotide in order to retrieve all mRNA via the terminal polyA sequences thereof. The oligonucleotide can then serve as a primer for cDNA synthesis, as described in International Patent Application WO90/11446.

According to one embodiment of the invention the PCR procedure will be continued, after initial two-stage amplification as described above, by replacing or supplementing at least one primer having such a distal DNA sequence or 'handle' by a third stage primer which hybridises to the handle so that on further amplification the third stage primer will be incorporated into the amplified target DNA. Such a third stage primer may advantageously be attached to a solid support or may carry means for attachment to a solid support or may carry a label or means for attachment of a label. As indicated above this third stage primer may advantageously be a standard DNA sequence which will remain the same in all assays irrespective of the target DNA. Both second stage primers may carry 'handles' and in the said third stage of PCR amplification one such primer may be replaced by a primer hybridising to its handle section and being attached to a solid support (or means for attachment thereto) while the other is replaced by a different primer hybridising to its handle and being attached to a label (or means for attachment to a label).

The label may be a radioactive atom such as $^{32}P$, $^{14}C$ or $^{3}H$ which may be incorporated into that one of said second pair of primers. Of course, it would be possible to incorporate a radioactive nucleoside into the last polymerisation step of the second PCR and thereby add a label to the second primer. The label may instead be a conventional enzyme or fluorescent substance attached directly to the primer or attached indirectly by, for example, an antibody which binds to the primer.

The means for attachment of the solid support or label may be affinity binding group such as biotin/avidin or streptavidin or an amino group or a terminal nucleoside which may interact with a carboxyl group or a CNBr-activated hydroxyl group on the solid support or label. Alternatively, the DNA handle may be capable of direct affinity binding to a protein.

A number of proteins are known which bind to specific DNA sequences and are often involved in genetic processes such as switching operons on and off. One such protein is the lac repressor lacI which reacts with the lac operon (lacOP) to inhibit transcription. Thus, if the handle attached to one of the primers in the process of invention is the DNA sequence lacOP, the solid support or label can be attached via the protein lacI. It is particularly convenient to devise a fusion protein of a DNA binding protein such as lacI with a further protein which is readily bonded to other molecules. One such further protein is protein A which readily reacts with IgG via the heavy chains thereof. Thus, a particulate solid support may be coated with IgG and thereby bonded to the above fusion protein. Similarly, an specific monoclonal antibody may be bonded to the protein A and used to bond selectively to a wide range of substances such as enzymic labels.

The concept of using the interaction between DNA and a DNA binding protein is of wider application beyond the PCR technique, due to the ease with which such an affinity bond can be broken under very mild conditions. Thus, for example, the bond between lacI and lacOP can readily be broken by reaction at room temperature with lactose, or more preferably with isopropylthiogalactoside (IPTG), while the bond between protein A and certain IgG's can readily be broken by e.g. lowering the pH to 3.0.

In general, it is preferred that one second stage primer carries a biotin group for attachment to a solid support via avidin or streptavidin, in view of the very strong binding thus provided. The other second stage process then preferably carries a DNA handle capable of binding to a specific protein such as LacI.

The specificity of the process for the target DNA is greatly increased by including the preliminary PCR amplification step before introducing one or more primers with handles. By such preliminary amplification, the concentration of target DNA is greatly increased with respect to other DNA and the further amplification with at least one primer specific to a different sequence of the target DNA, as described above, significantly enhances the signal due to the target DNA relative to the 'background noise'. As indicated above this concept of 'nested' PCR primers to achieve greater specificity has been described in the prior art relating to cloning of target DNA (Mullis, K. B. and Faloona, F. A., Methods in Enzymology (1987) 155, pp 335–350) but has not been applied to a system in which one or more primers were attached to a solid support on a label or to a DNA 'handle' permitting such attachment.

The amplification system of the present invention is particularly advantageous in diagnosis of pathological conditions characterised by the presence of specific DNA, particularly genetic diseases such as sickle cell anaemia, cystic fibrosis or α- and β-thalassaemia or latent infection by viruses such as herpes, hepatitis or HIV. Also, the method can be used with advantage to characterise or serotype bacterial and fungal infections where samples of the infecting organism maybe difficult to obtain or where an isolated organism is difficult to grow in vitro for subsequent characterisation as in the case of *P. falciparum* or *chlamydia* species. Even in cases where samples of the infecting organism may be easily obtained, the speed of the PCR technique compared with overnight incubation of a culture may make the method according to the invention preferable over conventional microbiological techniques.

The method of the invention also lends itself to subsequent processing steps after immobilisation. Thus, for example, if two stages of PCR provide double stranded DNA comprising the target DNA terminated with means for strongly bonding to an insoluble support at the 5'-end and a DNA handle for binding to a label via a protein such as LacI at the 3'-end, the amplified target DNA can readily be detected by means of the label, for example by an enzymatic colour reaction, and can then be subjected to strand separation to leave single stranded DNA immobilised on the inset support. The DNA thus immobilised can then be subjected to further operations. Thus for example, synthesis of a labelled second strand can be effected using a labelled primer at the 3'-end, whereupon strand separation liberates labelled ss-DNA into solution. Similarly, in vitro mutagenesis can be effected using an appropriate mutagenesis primer.

According to a particularly preferred embodiment of the invention, the immobilised single stranded DNA may be subjected to sequencing for example as described in International Patent Application WO89/09282 (the contents of which are hereby incorporated herein by reference) e.g. using the method of Sanger et al (Prox. Natl. Acad. Sci. U.S.A. 1977, 74, 5462–67). Furthermore, it is possible to omit the initial detection step and carry out sequencing on the immobilised single stranded DNA finally produced by the PCR amplification stages. In both cases, the provision of a universal handle at the 3' end of the ss-DNA enables a universal sequencing primer to be used while use of the nested primer technique greatly enhances the specificity of the method and reduces background 'noise' caused by non-specific binding.

While PCR amplification enables very small amounts of target DNA to be identified and abnormalities thus diagnosed, it is difficult to obtain quantitative information concerning the amount of target DNA present in a sample, due to uncertainty as to the true extent of amplification. Immobilisation of one end of the DNA and labelling of the other end enables the signal from the amplified DNA to be read after each cycle of PCR, or at intervals, thus providing data as to the extent of amplification at each stage. While the signal may be too low to be identified after the first one or two cycles, a plot of signal against PCR cycles can be extrapolated back to origin to give the initial amount of target DNA. Such as a procedure requires removal of the immobilised DNA from the medium, while the signal is read, followed by subsequent reintroduction. The immobilising primer is preferably attached to the support initially so that the whole PCR procedure is effected on the support. Magnetic beads provide a particular convenient form of support for this purpose The label is advantageously a radionuclide to permit rapid reading of the amount of immobilised label. As indicated above, the use of a universal handle for attachment of the label enables a universal radioactive label to be used.

The solid support may, for example, take the form of microtitre wells or dipsticks (e.g. plastic strips) which may be made of polystyrene activated to bind to DNA (K. Almer, Doctoral Thesis, Royal Institute of Technology, Stockholm, Sweden, 1988). Particles, fibres and capillaries made, for example, of agarose, cellulose, alginate, Teflon or polystyrene are especially convenient.

The PCR procedure according to the invention will normally be carried out in a conventional PCR buffer system. After the first phase of amplification using the outer pair of primers, it is advantageous, in addition to the new primer(s) for the second PCR phase, to add further PCR buffer to dilute the amplified product and any remaining primer molecules. In general, the dilution factor is advantageously large, for example in the range 20:1 to 200, e.g. about 100:1; however dilutions, e.g. as low as 1:1 are effective but may provide less selectivity.

The PCR buffer will generally be in the pH range 6.8 to 7.2, Tris/HCL is one suitable buffer. Strand separation is preferably effected at a temperature in the range 90°–95° C., annealing of primers in the range 45° to 55° C. and DNA synthesis in the range 65° to 75° C.

Particularly advantageously, the solid support comprises magnetic particles. Preferred magnetic particles are superparamagnetic beads produced by Dynal AS (Oslo, Norway). One of the second primer pairs may be immobilised on the magnetic particles; the particles may be already attached to the primer during the second PCR amplification stage or may be added subsequently to react with the biotinylated amplified target DNA.

Several advantages of the use of magnetic particles stand out clearly. The magnetic particles can be added to a mixture containing the target nucleic acid, e.g. a cell extract, stirred and then magnetically drawn to one side of the receptacle. The liquid can then be removed together with unwanted components and the magnetic particles, having the RNA bound thereto, can then be redispersed in a washing solution. The washing step can be repeated several times in quick succession. The whole process of obtaining the target nucleic acid can be performed in under 15 minutes.

A further advantage is the ease with which hybridisation or any process effected using the magnetic particles can be continuously monitored by magnetically aggregating the particles at intervals and assaying a label associated either with the material on the particles or with material in the supernatant.

The use of magnetic aggregation to separate the particles is far less vigorous than traditional separation techniques such as centrifugation which generate shear forces which can degrade nucleic acids or proteins.

The preferred particles are monodisperse and superparamagnetic and both these properties greatly assist the kinetics of reactions in which the particles are involved. It is a surprising feature of the invention that the probes carried by the particles react in the various reactions virtually as rapidly as if free in solution. Thus, for example, the total isolation of mRNA from a cell lysate using magnetic beads can be effected in about 15 minutes in contrast with the 2 hour period using an affinity column. By using monodisperse particles, that is particles of approximately the same size, the reaction rate and other parameters are particularly uniform. By using superparamagnetic particles (that is particles containing sub-particles of ferromagnetic material which are smaller than the domain size required to maintain permanent magnetism), one can avoid magnetic aggregation or clumping of the particles during reaction, thus again ensuring uniform and rapid reaction kinetics. Thus, the particles can readily be aggregated at a uniform speed onto a surface by application of a magnetic field but can readily be re-dispersed for a subsequent treatment step, e.g. by physical agitation. This uniformity of behaviour and rapidity of reaction lends itself particularly to automation, which is an essential requirement of many of the nucleic acid manipulations required in commercial production and/or repetitive processes. It is most important that the reactions and separations can be carried out completely reliably by an appropriate machine with minimal human intervention.

The preferred magnetic particles for use in this invention are monodisperse superparamagnetic beads produced according to EP 106873 (Sintef), the disclosure of which is incorporated herein by reference. In these beads, the iron is very uniformly distributed and provides a very uniform response to a magnetic field which is important in designing a reproducible procedure, particularly for automation, since all the beads move at the same speed. Furthermore, since a reproducible amount of iron can be incorporated in each particle, this can be adjusted to a relatively low level which permits the specific gravity of the particles to be in the range specified below. In the case of some less regular products, small particles either have too little iron to counteract Brownian forces completely when a magnet is applied or the specific gravity of the material leads to some undesirable sedimentation of the larger particles. Some automated systems use magnetic fields to restrain the particles within a reaction zone while solutions are passed through; uniform magnetic and rheological properties are essential in magnetic particles for use in such a system.

The term "monodisperse" used herein is intended to encompass size dispersions having a diameter standard deviation of less than 5%.

We prefer to use beads having a specific gravity in the range 1.1 to 1.8 most particularly 1.2 to 1.5. In the monodisperse beads used in accordance with the invention, the specific gravity is, again, particularly uniform, leading to uniform and predictable kinetic characteristics.

Advantageously, the monodisperse particles are spherical beads of diameter at least 1 and preferably at least 2 microns, being preferably not more than 10 and more preferably not more than 6 microns in diameter e.g. about 3 microns. Smaller particles sediment more slowly and in some cases the sedimentation time may be long compared to the reaction time, thus avoiding the need for physical agitation. However, particles of mean diameter 0.1 to 1.5 microns including fine particles of much smaller diameter behave less reliably in response to magnetisation.

The attachment of primers to the particles may be by direct chemical bonding as well as affinity binding, by streptavidin/biotin complexes and the like.

For attachment of the probes, the magnetic particles may carry functional groups such as hydroxyl, carboxyl, aldehyde or amino groups. These may in general be provided by treating uncoated monodisperse, superparamagnetic beads, to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

Preferred coated particles for use in the present invention may be prepared by modification of the beads according to the U.S. Pat. Nos. 4,336,173, 4,459,378 and 4,654,267, the disclosure of which is incorporated herein by reference. Thus, for example, macroreticular porous polymer particles, prepared from styrene-divinylbenzene and with a diameter of 3.15 microns were treated with $HNO_3$ to introduce —$NO_2$ groups at the surface of the pores. Then the particles were dispersed in an aqueous solution of $Fe^{2+}$. The $Fe^{2+}$ is oxidised by the —$NO_2$ groups which leads to precipitation of insoluble iron oxy-hydroxy compounds inside the pores. After heating the iron exists as finely divided grains of magnetic iron oxides throughout the volume of the porous particles. The $NO_2$ groups are reduced by the reaction with $Fe^{++}$ to $NH_2$ groups.

To fill up the pores and to introduce the desired functional groups at the surfaces, different monomers are caused to polymerize in the pores and at the surface. In the case of a preferred type of particle, the surface carries —OH groups connected to the polymeric backbone through —$(CH_2CH_2O)_{8-10}$ linkages. Other preferred beads carry —COOH groups obtained through polymerization of methacrylic acid.

Thus, for example, the $NH_2$ groups initially present in the beads may be reacted with a diepoxide as described in U.S. Pat. No. 4,654,267 followed by reaction with methacrylic acid to provide a terminal vinyl grouping. Solution copolymerization with methacrylic acid yields a polymeric coating carrying terminal carboxyl groups as in R452 beads referred to below. Similarly, amino groups can be introduced by reacting a diamine with the above product of the reaction with a diepoxide as in the R240, R442 and R469 beads, while reaction with a hydroxylamine such as aminoglycerol introduces hydroxy groups as in the M450 and L255 beads.

Dynabeads M450 (diameter 4.5 microns) which may be obtained from Dynal, Oslo, Norway have been coated with a monomeric epoxide, resulting in a mixture of epoxy and hydroxy groups. Contact with water however, converts the epoxy groups to hydroxy groups.

Dynabeads M-280 (diameter 2.8 microns) are polystyrene beads having hydroxyl groups which have been converted into tosyloxy groups by reaction with p-toluene sulphonyl chloride.

Using functionalised coatings of the above types, we have found the non-specific binding of DNA and/or RNA to be very low, particularly in the case of the carboxylated beads.

The primer may be attached to the magnetic particles via carboxyl groups, the DNA being firstly provided with a 5'-terminal amino group which can be made to form an amide bond with the carboxyl using a carbodiimide coupling agent. 5'-attachment of DNA can also be effected using hydroxylated magnetic particles activated with CNBr to react with 5'-amino DNA.

The 3'-attachment of primer DNA can also be effected by chemical synthesis. Here again, the very uniform nature of the monodisperse particles provides uniform reaction rates particularly suited to synthesis in an automated synthesiser such as the Gene Assembler (Pharmacia AS). The magnetic particle needs to be provided initially with a hydroxyl or protected hydroxyl group. Dynabeads M-280 of Dynal A/S are well suited to this purpose. If necessary, however, other surface functions such as carboxyl could be used to attach a linker carrying a hydroxyl group or alternatively a 3'-attached nucleotide.

5'-Attachment may be effected by coupling of 5'-aminooligonucleotides to tosyl-activated magnetic particles. The latter may be produced by tosylation of hydroxylated magnetic particles such as Dynabeads M-280 of Dynal A/S. Displacement of the tosyloxy group leaves the 5'-amino group directly attached to the magnetic beads.

Where the probe is merely to be used for mRNA isolation, however, the 3' end of the probe may be attached to the magnetic particles and this may be conveniently effected by forming a phosphoramidate linkage between the 3'-phosphate grouping of the DNA and an amino group on the particle.

Since biotin labelled nucleotides are commercially available, the 3'-end of DNA fragments can easily be labelled using DNA polymerase and these may be conveniently bound to avidin or streptavidin attached to the magnetic particles e.g. via a hydroxy group. The biotin label may be attached to the nucleotide by a spacer arm, such as one or more ε-aminocaproic acid moieties, to minimize steric hindrance. Thus, for example, a double stranded plasmid may be cut at a restriction site and end filled with biotinylated nucleotides, thus providing biotin at the 3'-end of each strand. If the linearised plasmid is then cut at another RE site, a section of double stranded DNA is excised and may be attached to streptavidin coated beads. Removal of the non-biotinylated strand leaves a biotin-attached oligonucleotide attached to the beads.

In general, the functionalisation of the beads and subsequent attachment of probes is advantageously such that each magnetic particle carries $10^3$–$10^6$ probes. (1–100 pmols per mg). The uniform size of the magnetic particles is of advantage in ensuring uniform probe density when the probes are reacted with the particles. Uniform probe density is important in ensuring that all the probes behave in substantially the same way in the various procedures in which they are used.

It is a remarkable feature of monodisperse, superparamagnetic particles that enzyme activity appears to take place very close to the particle surface e.g. within 7 bases. In the case of carboxylated Dynabeads beads it is found that the micro-surface of the beads is extremely irregular, presenting an unusually large surface area which may reduce steric hinderance to hybridisation and enzyme activity close to the surface. On the other hand the non-specific binding to such carboxylated beads is not increased.

The invention also comprises kits for carrying out the method of the invention. These will normally include at least the following components:

(a) a solid support such as a microtitre well or an array of such wells, a dipstick or beads, more preferably magnetic beads, the support carrying (i) means for attachment to amplified target DNA, (ii) means for attachment to a primer or (iii) a primer;

(b) a label carrying (i) means for attachment to amplified target DNA, (ii) means for attachment to a primer or (iii) a primer;

(c) a pair of outer primers and at least one inner primer provided with a DNA handle, where these are not attached to the support or label as in (a) or (b) above;

(d) a polymerase which is preferably heat stable, for example Taq1 polymerase;

(e) buffers for the PCR reaction; and (f) wash buffers for washing the support carrying immobilised DNA.

Where an enzyme label is used, the kit will advantageously contain a substrate for the enzyme and other components of a detection system.

Where the support is a dipstick, this may be provided with zones capable of interacting with several different target DNA molecules to enable simultaneous diagnosis of several abnormalities to be performed. Thus, such zones may carry primers specific to the respective target DNA.

The invention is illustrated by the following non-limiting Examples and Figures.

Figure 11:
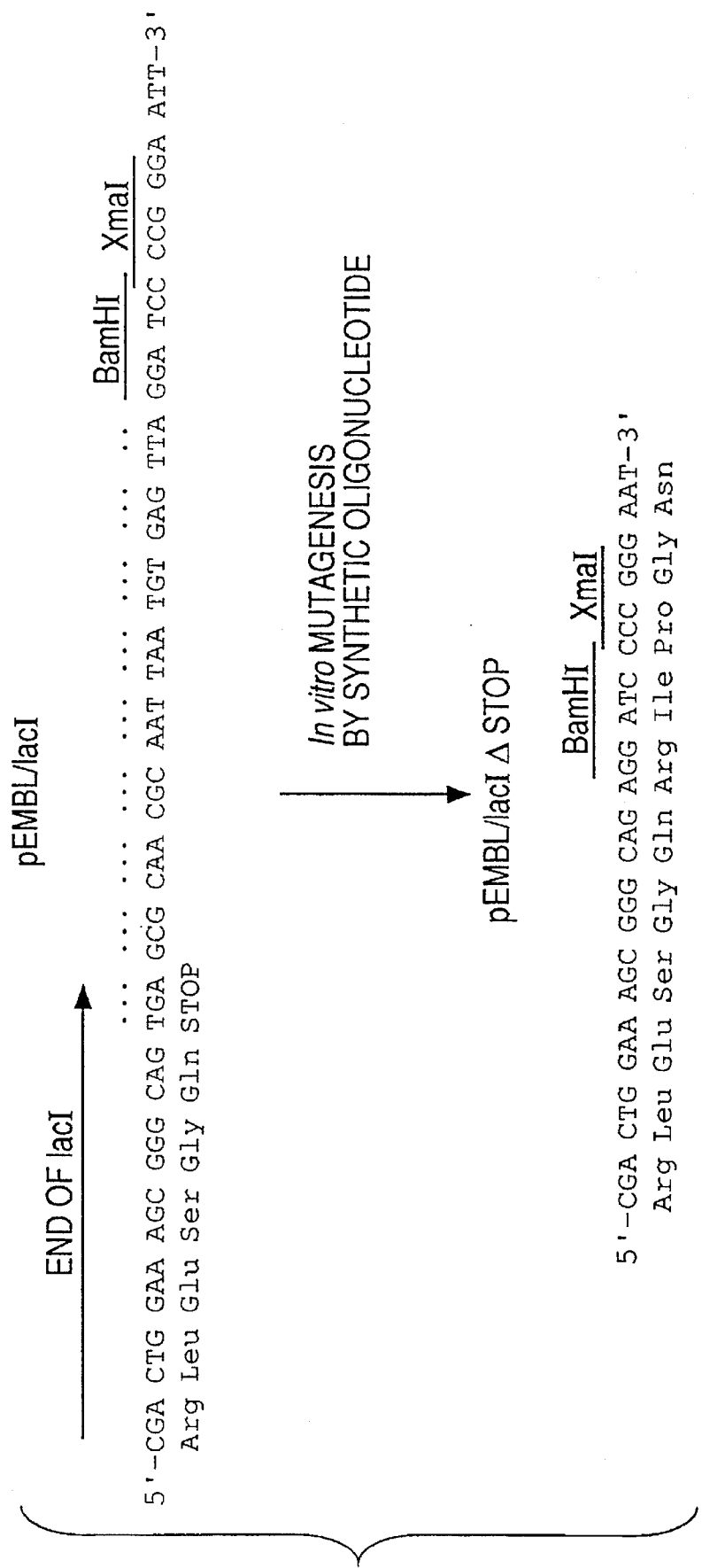

FIG. 11 shows schematically the mutagenesis of the lacI gene. (The sequences at lines 5 and 6 are also disclosed in SEQ ID NOS. 15 and 16; the sequences at lines 11 and 12 are also disclosed in SEQ ID NOS. 17 and 18).

Figure 12:
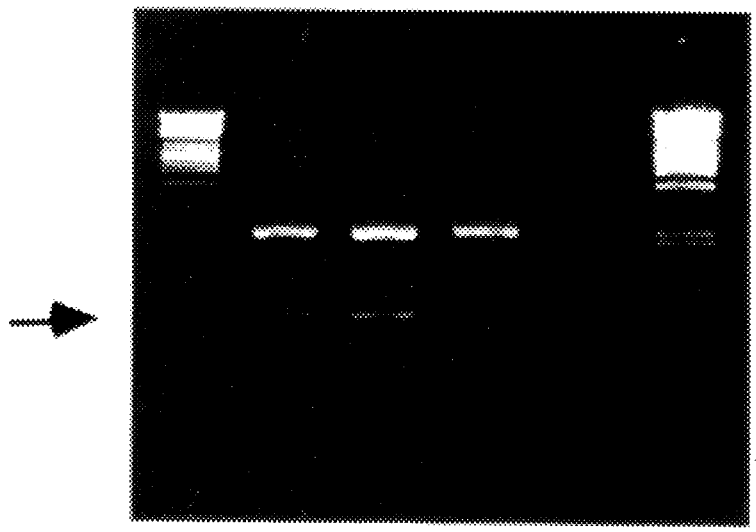

FIG. 12 shows an SDS-PAGE gel of samples from the immobilization and elution of a DNA fragment containing the lac operator sequence as described in Example 3(b).

Figure 13:
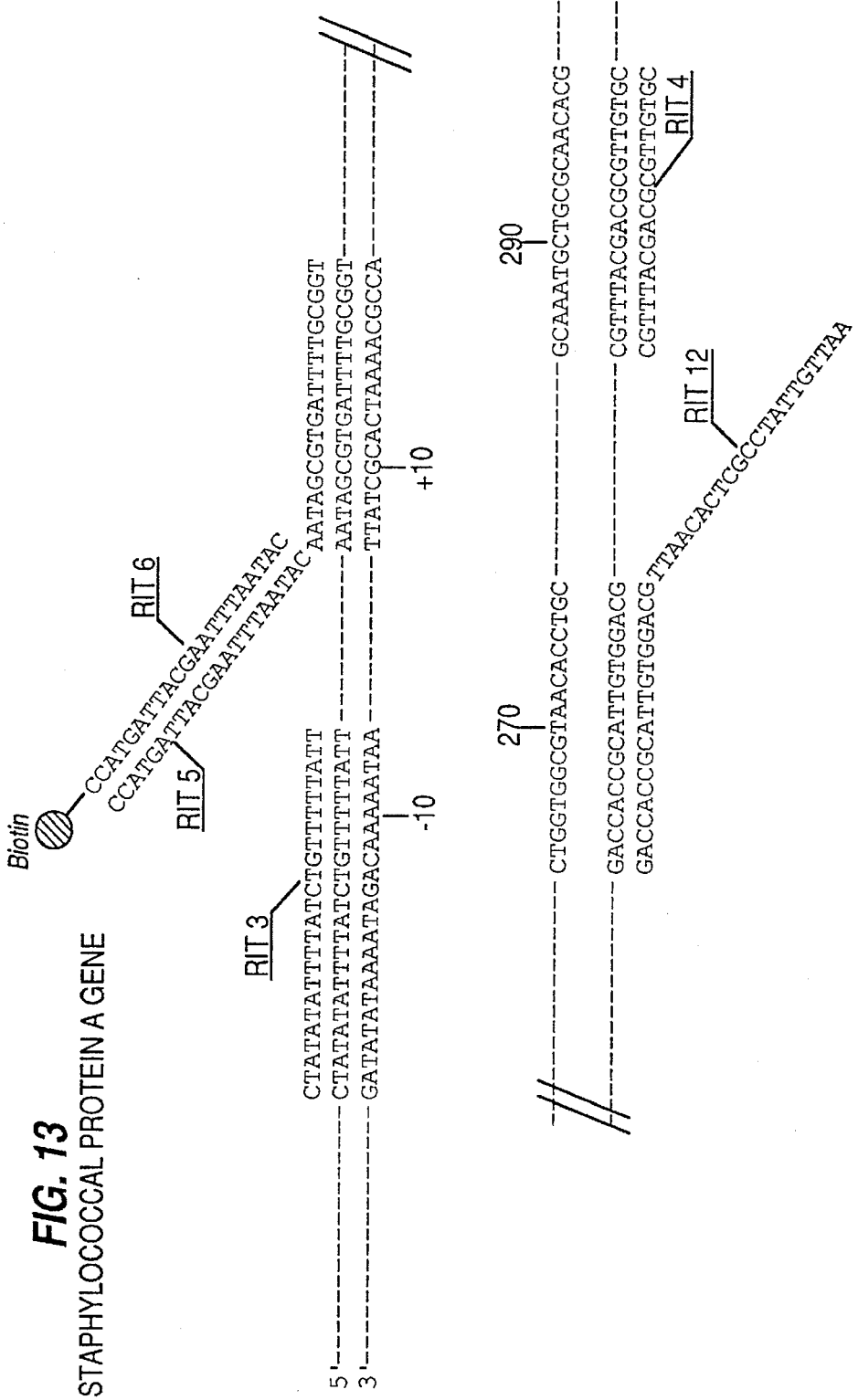

FIG. 13 shows some of the oligonucleotides (RIT3 is also disclosed in SEQ ID NO:3; RIT4 is also disclosed in SEQ ID NO:4; RIT5 is also disclosed in SEQ ID NO:5; RIT6 is also disclosed in SEQ ID NO:6 and RIT12 is also disclosed in SEQ ID NO:12) for S. aureus used in Example 3(c). The handle primer RIT12 contains the lac operator sequence (as does the RIT11 primer in FIG. 2) and RIT6 has a biotin 5'-end.

Figure 14:
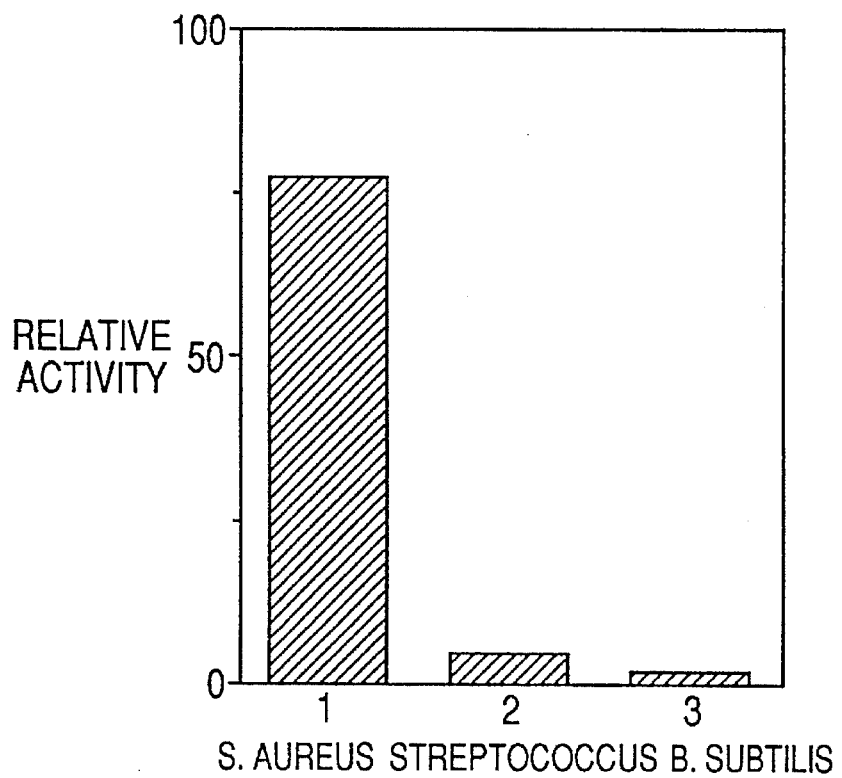

FIG. 14 shows the results of Example 3(c) in the detection of S. aureus using PCR amplified DNA and oligonucleotides specific for the staphylococcal protein A gene.

Figure 15:
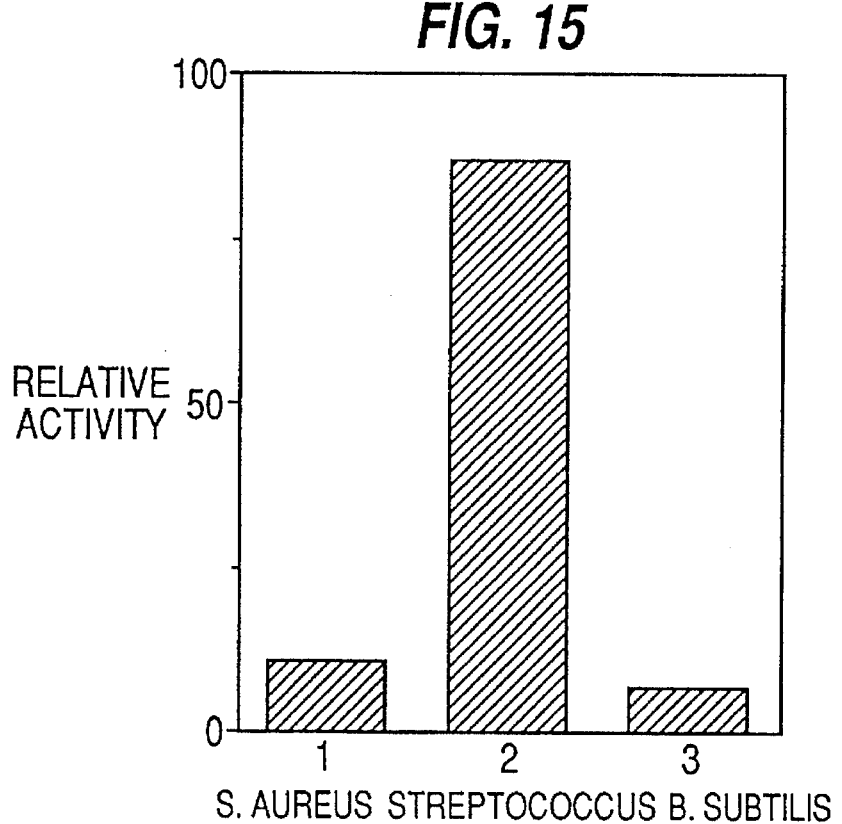

FIG. 15 shows the results of Example 3(c) in the detection of Streptocoocus G148 using PCR amplified DNA and oligonucleotides specific for the streptococcal protein G gene.

FIG. 16 shows the oligonucleotide primers (RIT33 is also disclosed in SEQ ID NO:26; RIT34 is also disclosed in SEQ ID NO:27; RIT35 is also disclosed in SEQ ID NO:28; RIT36 is also disclosed in SEQ ID NO:29; RIT6 is also disclosed in SEQ ID NO:36 and RIT43 is also disclosed in SEQ ID NO:30) used in Example 4 for the detection of the Pf155 gene of P. falciparum with the annealing site as described by Favaloro et al. (18)

FIG. 17 shows the results of Example 4(c) in the detection of P. falciparum. Number of parasites per sample as determined by microscopy is shown. The activity is determined as the colour change at 450 nm per minute.

FIG. 18 shows a schematic drawing outlining the DIANA concept for colorimetric detection of immobilized amplified nucleic acids followed by direct solid phase sequencing.

A lacI-lacZ fusion protein is used for the detection and magnetic beads as solid support.

FIG. 19 shows the sequence (SEQ ID NOS. 19 and 20) of the CrP target gene of *C. trachomatis* and the primers used for detection RIT23 (SEQ ID NO:22), RIT24 (SEQ ID NO:23), RIT 25 (SEQ ID NO:24) and RIT26 (SEQ ID NO:25) and sequencing (RIT43). Mutations determined by genomic sequencing of the clinical samples (FIG. 22) are indicated. The numbers refer to the nucleotides as described by Clark et al (20). Note that the sequence of primers RIT24 and RIT26 are complimentary to the sequence shown. RIT43 hybridises with the lac operator sequence (-TTAACACTCGCCTATTGTTAA-5', SEQ. ID NO:13) which is introduced in the second amplification.

Figure 20:

FIG. 20 shows an agarose gel demonstrating the binding of the amplified fragment to the beads and the size of the inner and outer fragment. Lanes 1 and 2 are from material from the second amplification and lanes 3 and 4 are from the outer fragment. Lanes 1 and 3 are from unbound material while lanes 2 and 4 correspond to the supernatant after the binding to the beads. The marker is λ DNA digested with Pst I. Note that the length of the fragments is the expected size (267 and 421 base pair respectively).

FIG. 21 shows the results of the DIANA assay on clinical chlamydia samples. The results of the clinical assay performed by a standard cell culture technique (35) is indicated (±). The activity of the DIANA is defined as described in Materials and Methods. Sample 8 is a positive control of cultivated *C. trachomatis* and sample 9 is a negative control for the PCR reactions (no DNA template was added to this tube).

Figure 22:
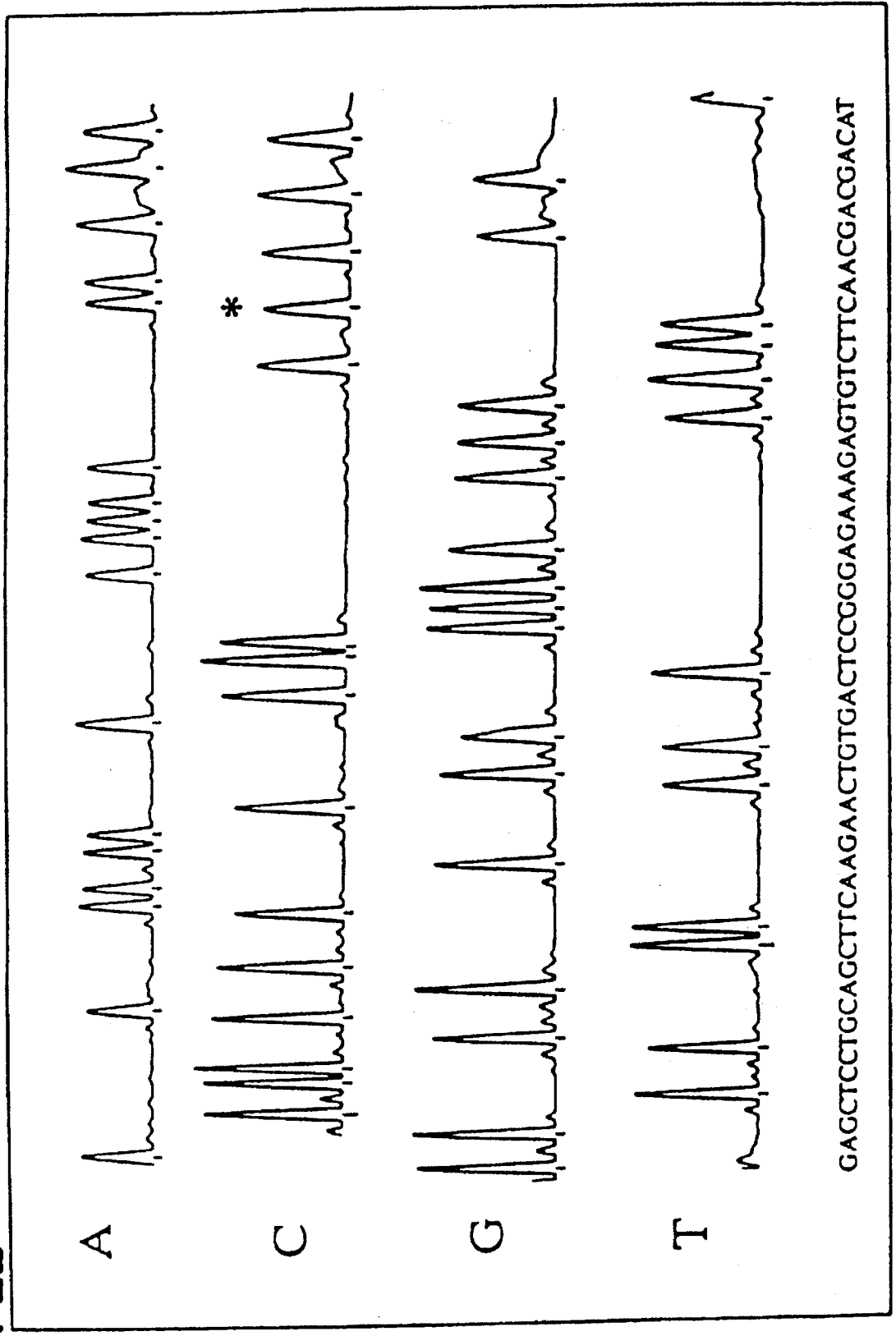

FIG. 22 shows the results (SEQ ID NO:21) of DNA sequencing of one (number 1, FIG. 21) of the positive chlamydia samples. The sequence was performed as described in FIG. 18 with a general RIT43 fluorescent labelled primer. The analysis was performed on an ALF automated laser fluorescent sequencer (Pharmacia, Sweden) as described by the manufacturer.

MATERIAL AND METHODS

Bacterial strains and plasmids.

*Escherichia coli* HB101 (1) and JM103 (2) were used as bacterial hosts. The plasmid vectors used were pSL1 (3), pEMBL9 (4), pDML1 (5), pNSEQ1 (6), pEZZT308 (7) and pSKS104 (8). M13K07 (9) was used as helper phage during mutagenesis. *Staphylococcus aureus* SA113 (10), *Streptococcus* G148 (11) and *Bacillus subtilis* 168 (12) were used in the Examples. These were grown as single colonies on TBAB-plates (Difco, U.S.A.) at 37° C. overnight.

A strain of *C. trachomatis* biovar L2 was kindly supplied by H. Gnarpe (Gävle Hospital, Sweden). Clinical samples were obtained with cotton-tipped swabs from male urethral (Karolinska Hospital, Stockholm, Sweden) and stored in PCR buffer (see below "PCR amplification") at +4° C. *Plasmodium falciparum* parasites from patient blood samples were prepared as described by Zolg et al., (13), and the microscopic analyses were preformed according to the giemsa stained blood smears method (14). The strains and plasmids have been deposited at the Department of Biochemistry, Royal Institute of Technology, Stockholm, Sweden.

Synthesis of oligonucleotides

Twelve oligonucleotide primers (RIT1-RIT12, SEQ ID NOS. 1–12, respectively), complimentary to the staphylococcal protein A gene or the streptococcal protein G gene (see FIGS. 1, 2 and 13), were synthesized by phosphoramidite chemistry on an automated DNA synthesis machine (Gene Assembler, Pharmacia, Sweden) as described by the manufacturer. Two of these primers (RIT1 and RIT6) was synthesized with an amino group in the 5-end, which was subsequently used to introduce a biotin-derivative (15) as described by the manufacturer (Pharmacia, Sweden). RIT2, RIT7, RIT11 and RIT12 were labelled with $\gamma^{32}$P-ATP (duPont, U.S.A.) using T4 polynucleotide kinase (Pharmacia, Sweden) as described in Molecular Cloning: a laboratory manual (16).

Four oligonucleotide primers (RIT23–26, SEQ ID NOS. 22–25, respectively) complementary to *Chlamydia trachomatis* (20), four primers complementary to *P. falciparum* (21) (RIT33–36, SEQ ID NOS:26–29, respectively) and a general sequencing primer (RIT43) were synthesized as described above. Two primers (RIT25, SEQ ID NO:24 and RIT43, SEQ ID NO:31) were synthesized with an amino group in the 5'-end, which was used to introduce a biotin (Clonetech, U.S.A.) and a fluorescent group (Pharmacia, Sweden), respectively, as described by the manufacturer. RIT25 and RIT43 were purified using a FPLC pepRPC 5/5 column (Pharmacia, Sweden).

DNA constructions

Restriction enzymes, T4 DNA ligase and Klenow DNA polymerase were used according to suppliers' recommendations (Pharmacia, New England Biolabs and Boehringer Mannheim). DNA work was performed as described earlier (16).

Protein and enzymatic assays

Cell extracts were obtained by sonication (18); the fusion protein, lacI-SPA, was purified by IgG affinity chromatography using IgG Fast Flow Sepharose (Pharmacia) as recommended and eluted, with 0.3M HAc, pH 3.3. Fractions were collected and lyophilized prior to SDS-PAGE analysis with a 3.5% stacking gel and a 13% separating gel; performed according to Laemelli (19). The gels were stained with Coomassie blue.

Recombinants containing a functional lacZ gene were assayed by plating on X-Gal (5-bromo-4-chloro-3-indolyl-β-D-galactoside) plates as described earlier (16). β-Galactosidase was assayed by as colorimetric procedure using ONPG (o-nitrophenyl-β-D-galactoside) in accordance with the supplier's recommendation. Alkaline phosphatase was assayed at 37° C. with 15.2 mM p-nitrophenyl phosphate (Sigma No. 104-0) as substrate in a buffer consisting of 0.1M glycine and 1 mM $MgCl_2$, pH 10.4. The streptavidin-alkaline phosphatase conjugate was supplied by Boehringer Mannheim.

PCR amplification

The in vitro amplification was carried out on a Techne Programmable Dri-block PHC-1 (Techne, UK). The general PCR solution was 1 mM of each of the primers, 200 uM of each dATP, dCTP, dGTP and dTTP, in a solution containing 67 mM Tris-HCl, pH8.8, 16.6 mM $(NH_4)_2SO_4$, 6.7 mM $MgCl_2$, 10 mM β-mercapto-ethanol and 170 ug/ml BSA under a layer of paraffin oil. A single colony was picked from the TBAB-plate with a sterile pasteur-pipette and put into a 0.5 ml microfuge tube (Kemila, Sweden) containing 10 ul of the PCR solution adjusted to pH 10 with NaOH. The tube was transferred to the temperature block and the cells were lysed with a 5 minute heating at 95° C. followed by cooling to room temperature. The solution was thereafter adjusted to pH 8.8 by adding an equal amount of a solution containing 67 mM Tris-HCl, pH7, 16.6 mM $(NH_4)_2SO_4$ 6.7 mM $MgCl_2$, 10 mM β-mercaptoethanol, 170 ug/ml BSA and 1 unit of TaqI DNA-polymerase (Stratagene, U.S.A.). A temperature cycle was started consisting of the following pro-gram: denaturation of template at 92° C. for 1 minute; annealing of primers at 50° C. for 2 minutes and extension of primers at 72° C. for 1 minute. After each fifth repeated cycle, 5 ul of solution was transferred to a new tube for binding to magnetic beads.

Binding to magnetic beads

Magnetic beads containing covalently coupled streptavidin were obtained from Dynal (Oslo, Norway). After the in vitro amplification using PCR, 5 ul of solution was added to a solution containing 10 ul 10 mM Tris-HCl, pH 7.5 and 1 mM EDTA with 158 ug of magnetic beads. The solution was incubated for 30 minutes at room temperature and non-bound DNA was removed by repeated washes with 35 ul of 5M NaCl followed by 10 mM Tris-HCl, 1 mM EDTA, pH 7.5. A neodymium-iron-boron permanent magnet (Dynal, Oslo) was used to hold the beads in the tube during this procedure. Before the final wash, the beads were transferred to a new tube to avoid background binding of radioactive label.

Detection of radioactive label

The tube containing the magnetic beads were transferred to a scintillation vial and the radiation was detected in a Scintillation Analyser (Packard, Tri-car 1500).

EXAMPLE 1

(a) Solid-phase PCR method using a single primer pair

Figure 1:
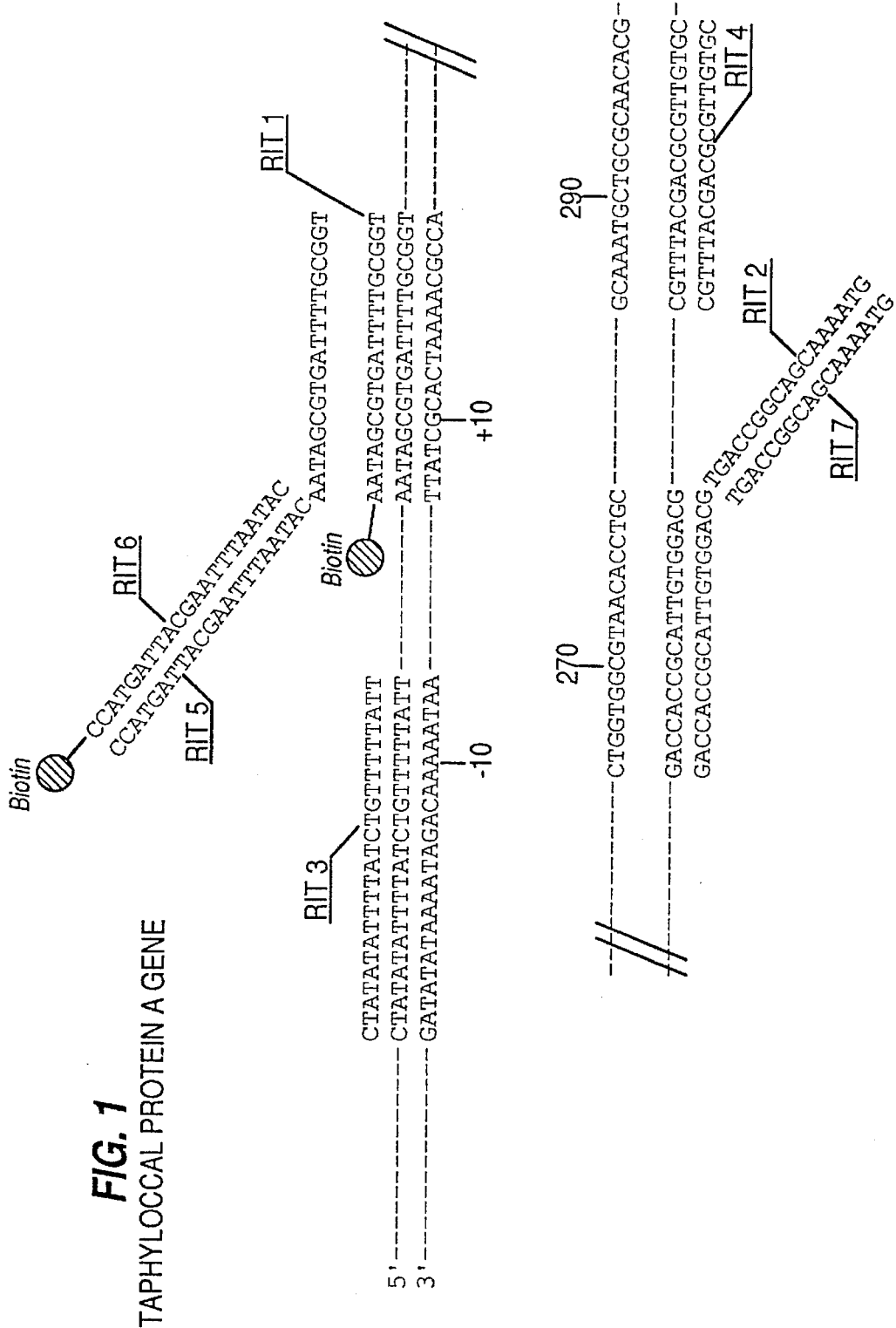
FIG. 1 shows the oligonucleotides RIT 1 (SEQ ID NO:1), RIT 2 (SEQ ID NO:2), RIT 3 (SEQ ID NO:3), RIT 4 (SEQ ID NO:4), RIT 5 (SEQ ID NO:5), RIT 6 (SEQ ID NO:6) and RIT 7 (SEQ ID NO:7), as used in Example 1.
Figure 3:
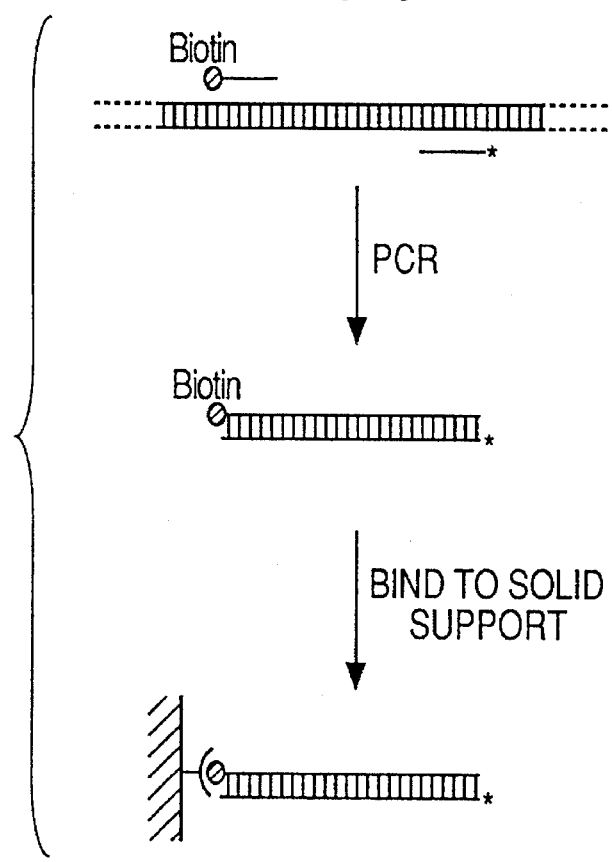
FIG. 3 shows diagrammatically the incorporation of biotin and a label into a sequence of target DNA as in Example 1(a).
Figure 4:
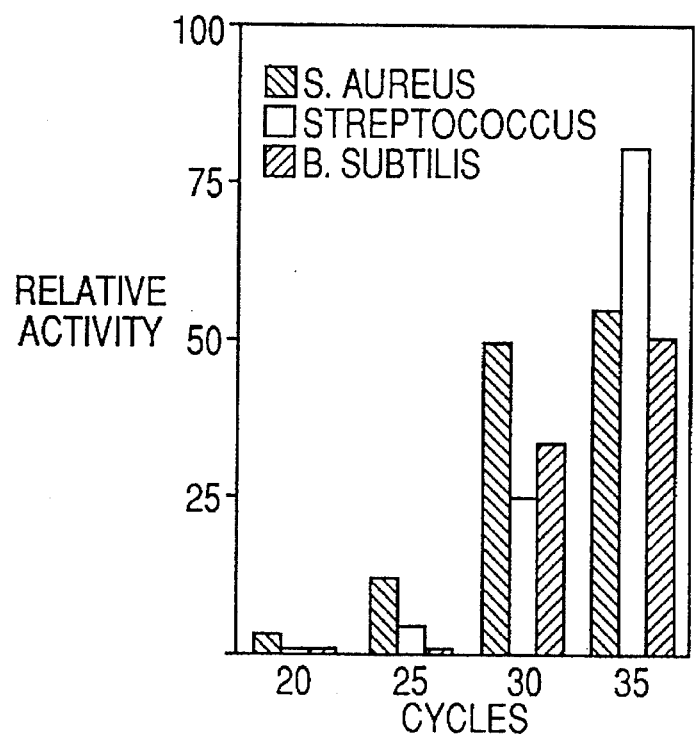
FIG. 4 shows the results for Example 1(a) as a plot of relative label activity against PCR cycles.

The experiment shown schematically in FIG. 3 was carried out using oligonucleotides RIT1 and RIT2 (FIG. 1, SEQ ID NOS. 1 and 2). RIT1 is biotinylated at the 5'-end, while RIT2 has been labelled at the 5'-end with $^{32}$P. Three sets of experiments using different bacterial cells were carried out using these primers specific for the staphylococcal protein A gene; first S. aureus cells containing the protein A gene and then two control cells, B. subtilis and Streptococcus, lacking this gene. The results for 35 cycles of PCR followed by immobilization to magnetic beads are shown in FIG. 4. As shown an increase of incorporated label is obtained during the PCR reaction. However, a high background is also obtained for the control samples (B. subtils and Stretococcus G148).

This example illustrates that the PCR can be used with a primer pair to incorporate label into the in vitro amplified DNA fragment. However, no or little specificity is obtained due to random extension of DNA or other chromosonal DNA.

(b) Solid-phase rested PCR method using two nested primer pairs

Figure 5:
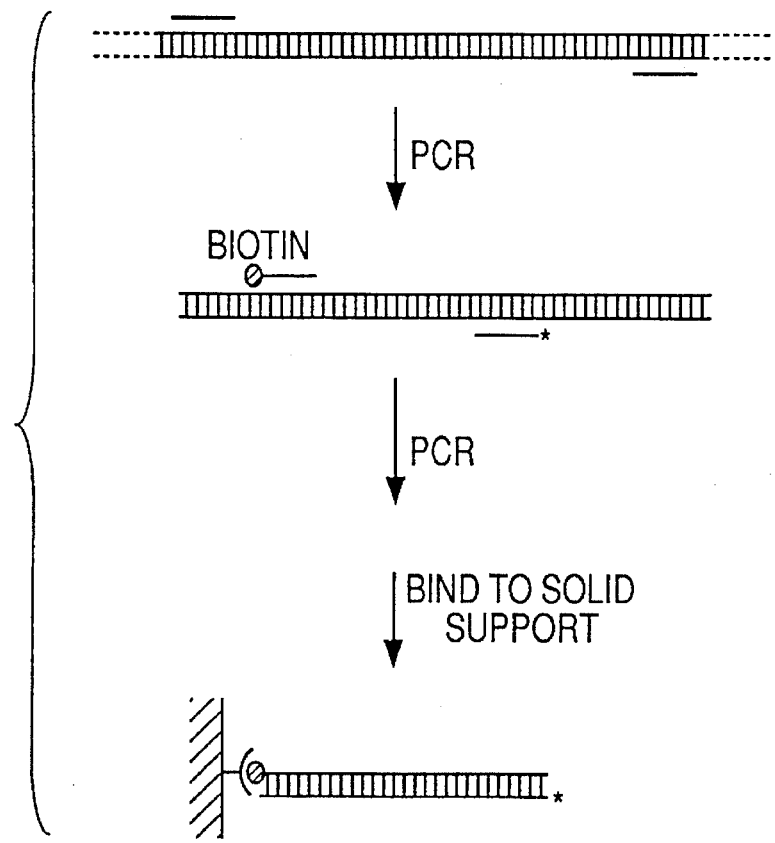
FIG. 5 shows diagrammatically the incorporation of biotin and a label as in Example 1(b).

Amplification of the specific DNA sequence was carried out according to the invention. The concept, designated dual polymerase chain reaction (D-PCR), is shown schematically in FIG. 5. A pair of primers specific for a sequence of the cell to be detected is used for a first round of in vitro amplification. After a suitable number of temperature cycles (e.g. 5 to 30 cycles), the sample is diluted e.g. 1:1 and a new primer pair is added. These primers are complimentary to internal parts of the primary amplified DNA fragment. The second pair has at the 5'-end either an affinity handle (such as biotin) or a label (such as an isotope). After additional PCR cycles, the amplified material is bound to a solid support and the label detected. The rationale behind the concept is that a high amount of specific template for the second PCR reaction is obtained during the first PCR reaction. This reduces the non-specific amplification of biotin and label containing DNA fragments as seen in example 1(a).

To investigate this concept as applied for specific detection of S. aureus, the oligonucleotides RIT3 and RIT4 (see FIG. 1) were used for the first PCR reaction. However, lower concentration of primers were used (0.2 mM of each primer) and only 25 temperature cycles were performed. After 25 cycles, the mixture was diluted 1:1 with the buffer solution containing nucleotides and additional 1 unit of Taq polymerase was added together with 1 mM of the oligonucleotides RIT1 (SEQ ID NO:1) and RIT2 (SEQ ID NO:2), having biotin and $^{32}$P at their respective 5'-ends. After various cycle times, 5 ul of PCR mixture was taken out and allowed to bind to magnetic beads carrying streptavidin.

Figure 6:
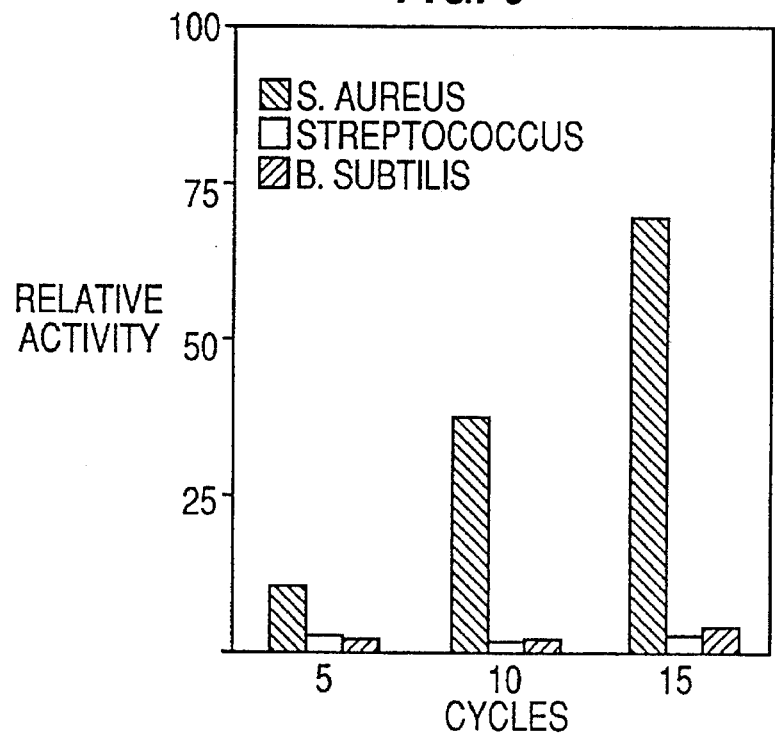
FIG. 6 shows the results of Example 1(b) as a plot of relative label activity against PCR cycles.

Detection of labelled beads for the different cycles are shown in FIG. 6. A low background label for the control cells (B. subtilis and Streptococcus G148), while a high degree of label is obtained for the specific cells (S. aureus).

This example illustrates that a high degree of labelling can be introduced into the PCR amplified material and that it can be detected using solid-phase technology described here. Low background label is achieved by the use of nested primers.

(c) Solid-phase nested PCR using handle sequence primers

Figure 7:
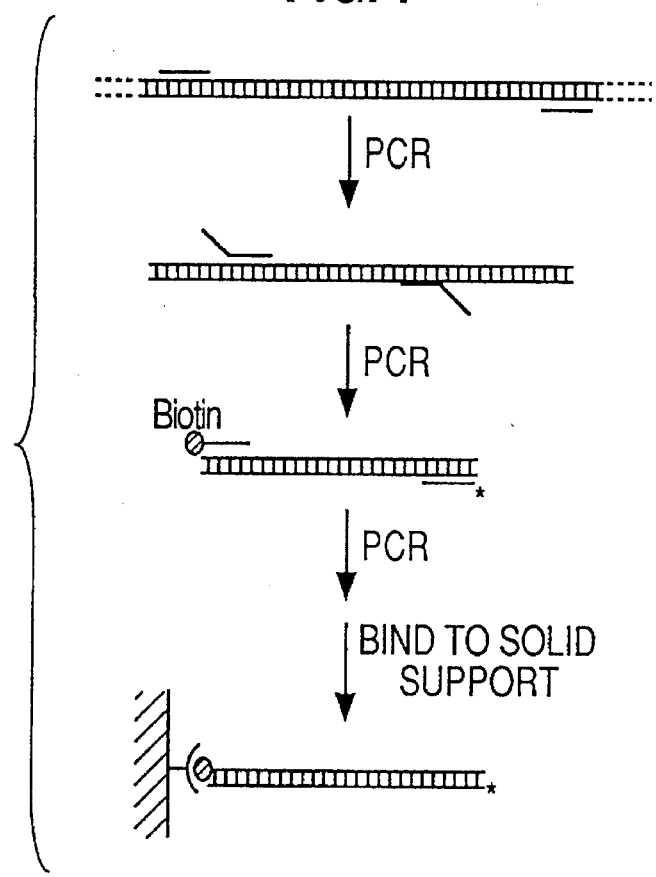
FIG. 7 shows diagrammatically the incorporation of biotin and a label as in Example 1(c).

A new approach to introduce solid support and label into the in vitro amplified material using a general primer pair is shown in FIG. 7. The dual-PCR approach described in 1(b) is used to amplify the sequence specific part of the DNA region. The second primer pair contains at each of their 5'-ends a specific handle sequence not complimentary to the DNA to be analyzed. In this way, the amplified material during the second PCR has the two different handle sequences introduced in the terminal regions (see FIG. 7). A third round of PCR using a general primer pair containing biotin and label, respectively, is thereafter performed. In this way, the amplified material becomes biotinylated and labelled. After binding to a solid support, the amount of bound label is detected.

To test this concept, S. aureus, B. subtilis and Streptococcus G148 cells were separately used for the in vitro amplification using the oligonucleotides shown in FIG. 1 (SEQ ID NOS:1–7). RIT3 (SEQ ID NO:3) and RIT4 (SEQ ID NO:4) were used for a first round of PCR as described in (b). After 25 cycles, the mix was diluted 1:1 with the buffer solution containing nucleotides and additional 1 unit of Taq polymerase was added together with 1 mM of the oligonucleotides RIT1 (SEQ ID NO:1), RIT2 (SEQ ID NO:2), RIT6 (SEQ ID NO:6), with biotin in the 5-end and RIT2 with $^{32}$P in the 5-end. After various cycle times, 5 ul of PCR mix was taken out and allowed to bind to magnetic beads containing streptavidin as described above.

Figure 8:
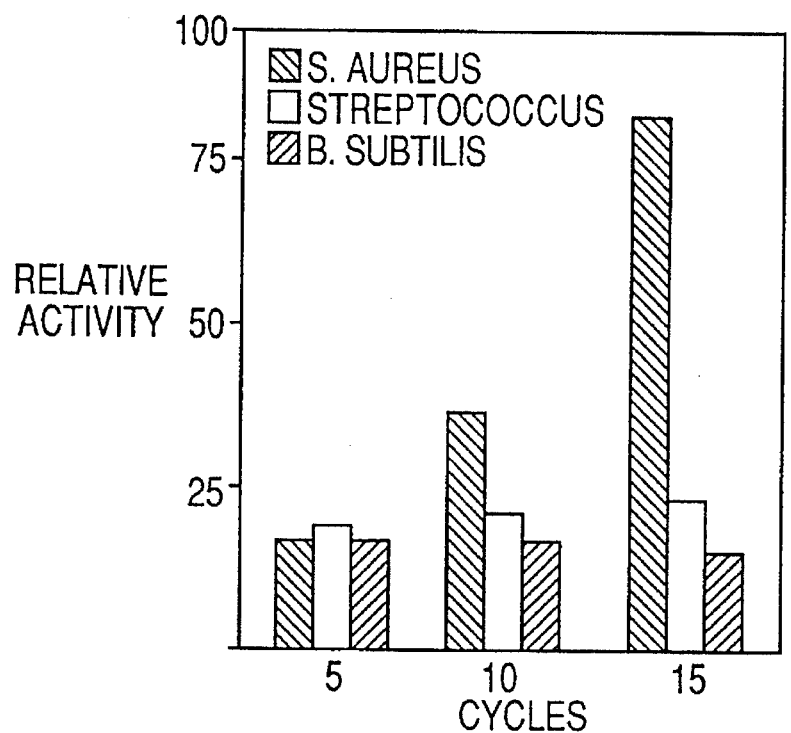
FIG. 8 shows the results of Example 1(c) as a plot of relative label activity against PCR cycles.

Detection of labelled beads for the different cycles are shown in FIG. 8. A relatively low background label for the control cells (B. subtilis and Streptococcus G148) is obtained, while a high degree of label is obtained for the specific cells (S. aureus) after 15 cycles.

This example illustrates that a high degree of label can be introduced into the PCR amplified material in a specific manner using general biotin and label primers. Low background level is achieved although the primers are not homologous with the DNA detected.

EXAMPLE 2

Figure 2:
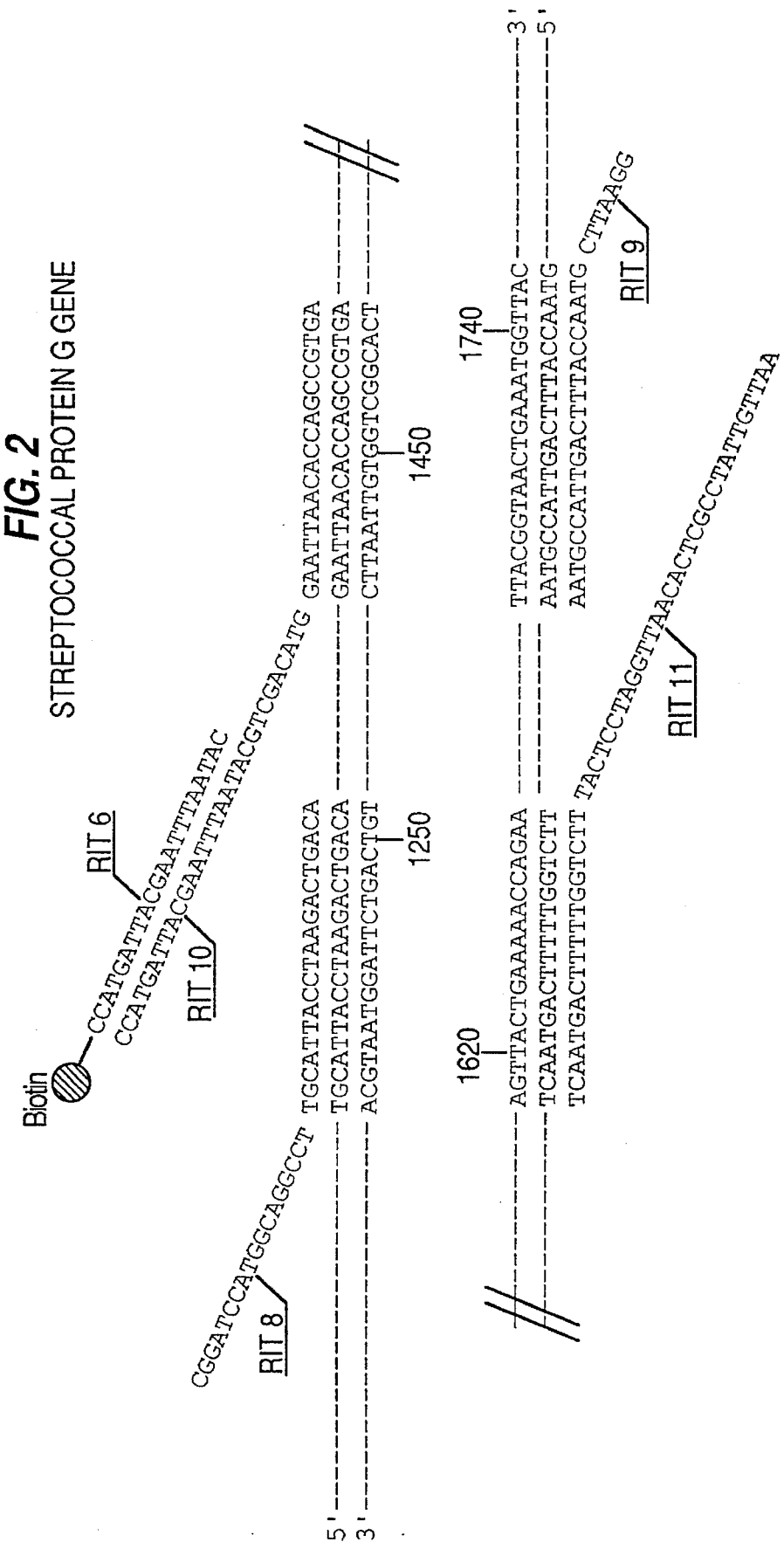
FIG. 2 shows the extra oligonucleotides RIT8 (SEQ ID NO:8), RIT9 (SEQ ID NO:9), RIT10 (SEQ ID NO:10) and RIT11 (SEQ ID NO:11), as used in Example 2 (RIT6 (SEQ ID NO:6) is also shown).

Solid-phase D-PCR detection of Staphylococci and Streptococci using the handle approach D-PCR detection of specific DNA using the handle approach was further tested using oligonucleotides specific for either the staphylococcal protein A gene (FIG. 1, (SEQ ID NOS. 1–7)) or the streptococcal protein G gene (FIG. 2 (SEQ ID NOS. 6,8,9,10, and 11)). Cells of either S. aureus SA113, B. subtilis 168 or Streptococcus G148 were analyzed by both sets of oligonucleotides.

The detection of the *S. aureus* gene was carried out as described in Example 1 except that the second round of PCR contained only three oligonucleotides; RIT5 (SEQ ID NO:5) RIT6 (SEQ ID NO:6) with biotin and RIT2 (SEQ ID NO:2) end labelled with $^{32}$P. The detection of the Streptococcus gene was carried using the same scheme as described above using primers RIT8 (SEQ ID NO:8) and RIT9 (SEQ ID NO:9) for the first round of PCR (25 cycles) and RIT10 (SEQ ID NO:10), RIT6 (SEQ ID NO:6) with biotin and RIT11 (SEQ ID NO:11) end labelled with $^{32}$P for the second round of PCR. The second round of PCR was terminated after 15 cycles and the amplified material was allowed to bind to streptavidin coated magnetic beads as described in Example 1.

Figure 9:
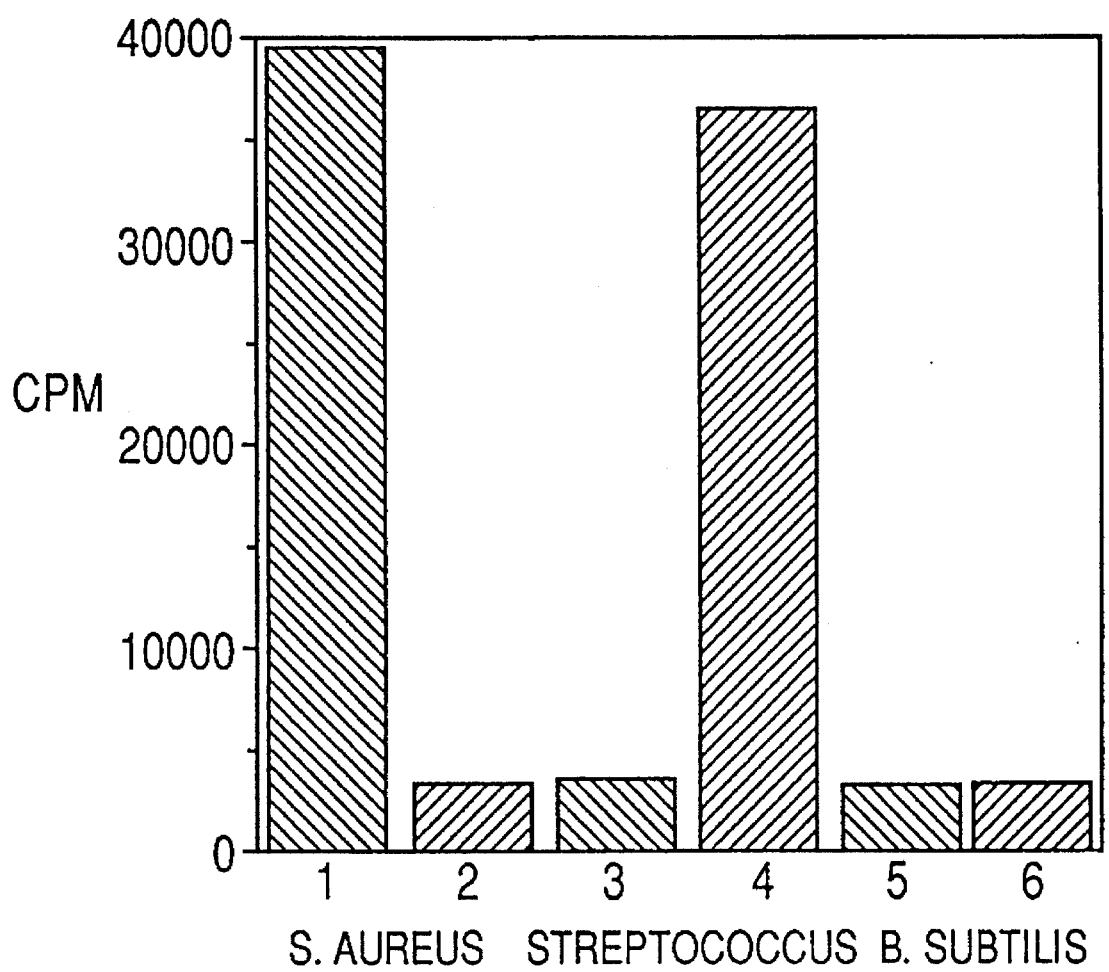
FIG. 9 shows the results of Example 2 as a plot of relative label activity against PCR cycles.

The results of the assay is shown in FIG. 9. A relatively low background label is obtained for the control cells using both sets of oligonucleotides S. aureus specific oligonucleotides shown as filled bars and Streptococcus specific oligonucleotides shown as striped bars). For both sets of primers, a significant amount of label is introduced in the in vitro amplified material when the specific cells are analyzed. This example illustrates that the concept can be used for detection of two different bacteria using the same general biotinylated handler primer in both assays.

EXAMPLE 3

Figure 10:
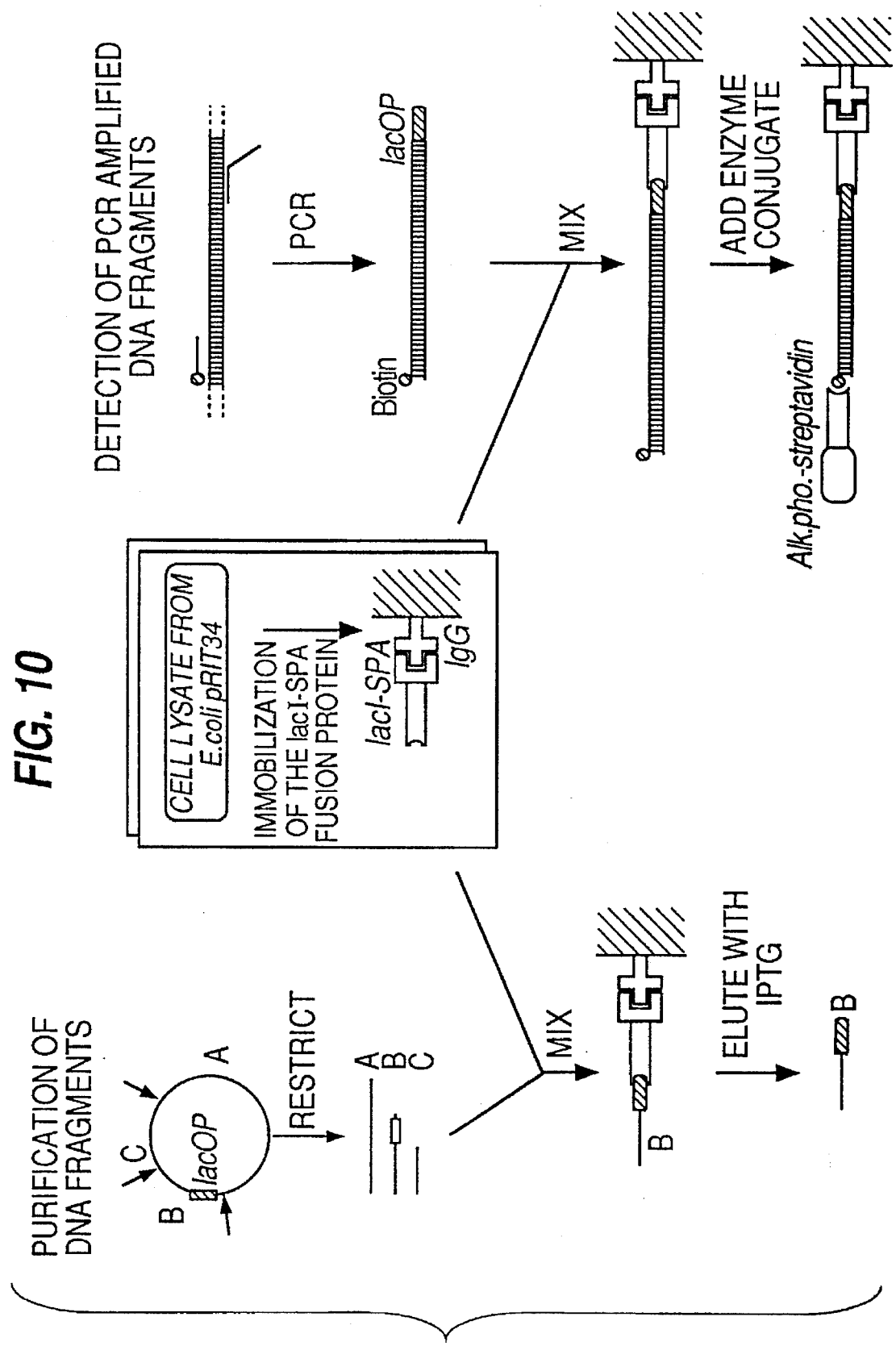
FIGS. 10A and 10B show schematically the use of a DNA-binding fusion protein in the purification (A) and in the detection (B) of DNA fragments.

This Example concerns the use of a DNA-binding protein to purify DNA fragments and in the detection of PCR amplified fragments as shown schematically in FIG. 10.
(a) Construction and analysis of a DNA-binding fusion protein A gene fusion comprising the staphylococcal protein A (SPA) gene and the *E. coli* lacI gene encoding a DNA-binding repressor molecule was constructed. To enable in vitro mutagenesis of the stop codon at the end of the lacI gene (thus creating a open reading frame) the gene was first cloned into pEMBL9. The donor plasmid pSI.1 was digested with PstI and BamHI giving a fragment of 1361 bp, including the lacI gene of 1080 bp, which was isolated and inserted between the same sites in the mp 9 linker of pEMBL9.

After transformation, *E. coli* JM103, was spread on plates consisting of ampillicin, X-Gal and IPTG, and white colonies were isolated. Single strand plasmid DNA, pEMBL/ lacI, was obtained by transforming plasmid DNA from one of these colonies into JM103 using the packing deficient helper phage M13K07 to infect and to pack single stranded DNA with the pEMBL-vector carrying the organ of replication from phage f1. By the use of a synthetic oligonucleotide, (5'-ATTCCCGGGATCCTCTGCCOGCTTTCCAG-3', SEQ ID NO:14) a mismatch priming on the single strand template was performed. The primer extension conditions were essentially as described by Carter (17). The extended material was used to transform *E. coli* JM103. The mutant plasmids, pEMBL/lacI STOP, were selected by blue colonies on agar plates containing ampicillin, X-Gal and IPTG. FIG. 11 shows the in vitro mutagenesis schematically; the nucleotides indicated by asterisks are those which are deleted during the mutagenesis.

The 3'-end of the mutated lacI gene without the stop codon was released with EcoRV and Xma from plasmid pEMBL/lacI STOP yielding a fragment of 291 bp. The isolated fragment was ligated into pDMI.1, which had been digested with the same restriction enzymes. The pDMI.1 plasmid consists of three major elements: a lacI$^q$ gene overproducing the lac repressor, the gene for neomycin phosphotransferase conferring resistance to kanamycin and the p15A replicon. The resulting construction, pDMI.1 STOP, thus encodes mutant lacI. A fragment encoding a part of protein A was cleaved out from the pNSEQ1 vector with BamH1 and isolated. This fragment was then inserted into a unique BamH1 site in the 3'-end of the lacI-gene in plasmid pDMI.1 STOP plasmid. This new plasmid, pRIT34, encodes the lacI-SPA fusion gene of 1926 bp. *E. coli* strain HB101 harbouring the plasmid pRIT34 was grown over night in baffled Erlenmeyer-flasks containing Tryptic Soy Broth (30 g/l) (Difco, U.S.A.) with an addition of Yeast Extract (7 g/l), and kanamycin (50 mg/l). The fusion protein, with a molecular weight of 70.6 kDA (deduced from the amino acid sequence) was purified from sonicated cells using affinity chromatography on matrix-bound IgG. After elution and lyophilizing the affinity-purified proteins were analyzed by SDS-PAGE. The production level was approximately 20 mg/l culture. Almost 90% of the affinity purified protein was found to be full-length.

This example illustrates that a lacI-SPA fusion protein can be produced in a recombinant host and that the fusion protein can be immobilized and purified on a solid support containing covalently bound IgG.
(b) Purification of DNA fragments Plasmid DNA of pEZZT308 was digested with HgiAI and NotI, yielding fragments of different length: 85, 497, 676, 1161 and 1183 bp. The fragment of 676 bp contained the lac operator sequence. After dilution of the digested DNA to a concentration of 140 ng/ul it was divided into 3 aliquotes. IgG-Sepharose was mixed with lysates of HB101 harbouring pRIT34 for 1 hour at room temperature. The lacI-SPA fusion protein present in the lysate became immobilized on the IgG-Sepharose via the SPA moiety. After extensive washing with a washing buffer consisting of 0.1M Tris, 0.15M NaCl and 0.1% BSA, pH 7.4 to eliminate excess fusion protein, 100 ul of the immobilized lac-SPA fusion protein was mixed at room temperature with 100 ul of digested DNA from plasmid pEZZT308. Analysis of the supernatant revealed that the 676 bP fragment had selectively bound to the gel (FIG. 12), lane 3).

After repeated washing, followed by incubation at room temperature for 45 minutes with 1 mM IPTG, resulted in elution of the fragment (FIG. 12, lane 4). As shown in FIG. 12 (lane 1 and 2), the negative controls using IgG-Sepharose without lysate (lane 1) or IgG-Sepharose mixed with lysates from HB101 harbouring pDMI.I (lane 2), yield no or little binding of the specific DNA to the column. (Lane M shows marker DNA)

This illustrates that the DNA-binding part of the fusion protein is functional after immobilization to the solid support through the protein-A-IgG complex. It shows that a fragment can be immobilized to the column and eluted with an IPTG solution in manner schematically outline in FIG. 10.
(c) Detection of PCR amplified DNA fragments The use of the PCR technique has made it possible to generate multiple copies of target DNA from only one DNA template. We have designed and described above oligonucleotides which are capable of hybridizing to specific DNA of the genomes of *S. aureus* and Streptococcus G148 and have shown their species specificities by reference to, e.g. *B. subtilis*. The dual-PCR approach, i.e. using with two sets of nested primers, can be used to reduce amplification of non-specific DNA fragments as shown above. Below we describe a first amplification of 25 cycles with flanking primers, followed by amplification of 15 cycles, using nested handle primers for immobilization and detection. The handle primers were: RIT6 (SEQ ID NO:6) with biotin in 5'-end, RIT11 (SEQ ID NO:11) and RIT12 (SEQ ID NO:12) with the lac operator sequence. The primers used are schematically shown in FIGS. 2 and 13. The PCR amplification was carried out as described in Example 2.

The procedure used is shown schematically in FIG. 10B. Immobilization of the lacI-SPA fusion protein to IgG-Sepharose was carried out as described in Example 3(b), except that the washing buffer consisted of 0.1M Tris, 0.15M NaCl, 0.1% Tween 20, 1 mM MgCl$_2$ and 0.1 mM ZnCl$_2$. 100 ul of IgG-Sepharose carrying the immobilized fusion protein was mixed with 20 ul of amplified PCR-mixture (diluted with washing buffer to 500 ul) for 60 minutes at room temperature. The amplified DNA is bound to the Sepharose by the interaction of the lac operator sequence of the handle with the lacI part of the lacI-SPA fusion protein. The sepharose beads were then washed 3 times with 1.5 ml of buffer. Detection of bound amplified DNA was carried out by the addition of 100 ul of streptavidin-alkaline phosphatase conjugate to the mixture which was left to stand for 30 minutes. The streptavidin-alkaline phosphatase is bound to the amplified DNA via the 5' biotin, as shown in FIG. 10B. Excess of conjugate was eliminated by three washings with 1.5 ml of washing buffer. 500 ul of alkaline buffer was then added, the temperature adjusted to 37° C., and then 500 ul of substrate was added. The enzyme reaction was stopped with 40 ul 0.5M NaOH and the activity measured (by change of absorbence per second at 405 nm) using a spectrophotometer.

FIGS. 15 and 16 show the results of using either oligonucleotides specific for *S. aureus* (FIG. 14) or oligonucleotides specific for Streptococcus G148 (FIG. 15). A high degree of colour change above a background level is achieved for both oligonucleotides. This illustrates that the immobilized fusion protein can be used to recover DNA fragments containing the lacI operator, that the bound DNA molecules can be detected by a simple colour reaction and that the same immobilizing fusion protein colour reaction can be used in the detection of different amplified DNA fragments.

EXAMPLE 4

This example demonstrates that an infectious agent of great clinical importance could also be detected, the DIANA was used to determine the presence of *Plasmodium falciparum* DNA in clinical blood samples.

The two step PCR procedure outlined in FIG. 10 was carried out using the five oligonucleotides shown in FIG. 16, and SEQ ID NOS. 6 and 26–30. The *P. falciparum* specific primers hybridize to the 5'-end of exon II in the Pf155/RESA gene (21). This gene codes for a parasite antigen, considered to be one candidate for a future malaria vaccine (22,23). The Pf155/RESA gene has only been characterized in two parasite strains earlier (21). The 5' region of the gene was chosen because it is thought to be relatively conserved in different strains, although it might contain minor variations. The first set of primers generates a 428 bp fragment and the second set a 398 bp fragment in the earlier characterized strains.

The two step PCR amplification was carried out on 14 samples obtained from patients in The Gambia, Africa as described in Example 3. The resulting material was captured in the LacI containing sepharose (Example 3) and detected via the streptavidin-alkaline phosphatase conjugate. The results of the assay are presented in FIG. 17. Note that samples from patients with low grade parasitemias were included in the study, to investigate the sensitivity of the assay. All the samples positive by microscopy, were also positive in the DIANA, using only 1 μl sample volumes. 10 parasite genomes could reproducibly detected, with a distinct signal significantly over background.

EXAMPLE 5

This example describes a system for rapid colorimetric detection of specific genomic DNA fragments amplified by the polymerase chain reaction (PCR) which has been designed to allow for direct solid phase sequencing of positive samples. The amplified material is immobilized to magnetic beads using the biotin streptavidin system. A lac operator sequence is incorporated in the amplified material during the second step of a nested primer procedure. This 21 base pair sequence is used for a general colorimetric detection with a fusion protein consisting of the *Escherichia coli* lac repressor and β-galactosidase. Positive samples can subsequently be treated with alkali to obtain a single stranded DNA template suitable for direct genomic sequencing. This method to detect immobilized amplified nucleic acids (DIANA) is well adapted for automated or semi-automated clinical assays. Here, we show that it can be used to detect and sequence *Chlamydia trachomatis* genomic DNA in clinical samples.

(a) The basic concept

The approach for the detection and sequencing of specific in vitro amplified material using a magnetic bead as a solid phase is shown in FIG. 18. The first step is a standard PCR with oligonucleotides specific for the target DNA sequence. A large number of cycles, i.e. 25–35 cycles, are performed to obtain many template molecules that can be used in the second PCR step. for samples lacking the target DNA, a non-specific amplification of random DNA will occur as described earlier. The material obtained after the first PCR step is diluted and subsequently used for a second PCR with the inner primers, which are specific for a sequence within the DNA fragment amplified in the first step. One of the primers is biotinylated, while the other contains a lac operator "handle" consisting of 21 nucleotides. Thus, successful amplification yields specific DNA with biotin and lac operator incorporated in the fragment. The second PCR reaction is carried out with fewer cycles, 15, and therefore very low yield of fragments containing biotin and lac operator will be obtained for samples containing non-specific DNA (FIG. 18).

The biotinylated material is thereafter captured on magnetic beads coupled with streptavidin using interaction between biotin and streptavidin. Thus, non-biotinylated fragments can easily be removed. A recombinant fusion protein consisting of the lac repressor (lacI) and β-galactosidase (lacZ) is added to the beads and bound enzyme conjugate is detected by adding chromogenic substrate, specific for the β-galactosidase enzyme.

The samples identified as positive using this colorimetric procedure can directly be treated with alkali to remove the bound fusion protein and to melt the double stranded DNA immobilized to the beads. The biotin streptavidin complex is resistant to this treatment and thus a single stranded template suitable for sequencing is obtained using this one-step elution procedure. A solid phase DNA sequencing protocol (24) can therefore be followed without the need for extra template preparations. The extended material is finally eluted from the beads using formamide and loaded on a sequencing gel. The solid phase method provides a clean template (24) which ensures that reproducible sequence information is obtained without the need for precipitations, centrifugations or desalting procedures.

(b) Design of the synthetic primers *Chlamydia trachomatis* is Gram negative bacteria characterized by an obligatory parasite life cycle within eucaryotic host cells. On the basis of clinical, biological and molecular characteristics, the human C. trachomatis isolates have been grouped in two biovars and 15 serovars (25,26) Serovars L1, L2 and L3 are clinically important as they are associated with relatively invasive from of chlamydia disease involving lymphold tissue (27).

Several genes from serovars L1 and L2 of C. trachomatis have been isolated and characterized. This includes the major outer membrane protein (MOMP) from serovar L1 (28) and L2 (29) and the outer membrane cysteine rich protein (CrP) from serovar L1 (20). We decided to perform a DIANA assay, as described in FIG. 18, with C. trachomatis as a model system using the sequence of the CrP gene as target DNA. The Cr protein has been suggested to be necessary for the structural integrity of the chlamydial elementary body envelope (30), which makes the protein particular important given the apparent absence of peptidoglycan of C. trachomatis (31). Therefore, this gene is most likely essential for invasive chlamydia and a potential candidate as a target for detection of chlamydial DNA in clinical samples.

Four oligonucleotide primers specific for the middle part of the CrP coding region of C. trachomatis serovar L2 were synthesized. The sequence of the four primers are shown in FIG. 19 (and SEQ ID NOS:22–25) where also the location of the target DNA within the CrP gene is shown. The two outer primers hybridize 421 base pairs from each other, while the inner primers are 267 base prais apart. Biotin was covalently coupled to one (RIT25, SEQ ID NO:24) of the inner primers, while the 21 base pair handle corresponding to the E. coli lac operator sequence (see Material and Method for details) was added to the 5'-end of the other inner primer (RIT26, SEQ ID NO:25).

Immobilization of the PCR amplified material on magnetic beads.

To test the efficiency of the primers designed to amplify the chlamydia CrP coding region, a culture of C. trachomatis serovar L2 was used for a standard agarose assay. Cells were directly lysed in the PCR buffer and the CrP gene was amplified for 25 cycles using the outer primers (RIT23 and RIT24, FIG. 19, SEQ ID NOS:22 and 23). After a 100-fold dilution of the obtained material, a second PCR step was performed for 15 cycles using the inner primers (RIT25 and RIT26, FIG. 19,SEQ ID NOS:24 and 25). The PCR buffer used contained 20 mM TAPS (pH=9.3), 8 mM$MgCl_2$ and 0.2% Triton X. The clinical tops were put into PCR tubes filled with PCR buffer (10 μl) and rubbed against the wall of the tube. The tube was subsequently heated to 99° C. for 5 minutes in order to lyse the cells and then cooled on ice. The lysed mixture 90 μl of a PCR buffer with 0.2 mM dNTP, 0.2 mM of each primer and 1.0 units of Taq polymerase (Boehringer Mannheim, Sweden) was added. One temperature cycle on the PCR was: denaturation of template 95° C., 0.5 minute; annealing of primers 58° C., 1 minute; extension of primers 72° C., 1 minute.

The material after the first and the second PCR step, respectively, was mixed with magnetic beads containing streptavidin and the supernatant was analyzed by agarose gel electrophoresis.

Magnetic beads with covalently coupled streptavidin, Dynabeads M280-Streptavidin (31) was obtained from Dynal (Norway). A neodymium-iron-boron permanent magnet (Dynal, Norway) was used to sediment the beads during washing procedure. 300 μg of the beads was mixed with 85 μl of the PCR mixture and incubated for 20 minutes at room temperature. The beads was then extensively washed using the TST buffer, described above.

The results (FIG. 20) shows that the first PCR yields a specific band (lane 3) of the expected size (421 base pairs), which does not bind to the magnetic beads (lane 4). In contrast, the shorter sized (267 base pairs) material obtained after the second PCR step (lane 1) is efficiently captured by the magnetic beads (lane 2). More than 95% immobilization yield is achieved, which demonstrates the efficiency of the biotin-streptavidin system for capturing DNA on a solid support.

(c) Purification of a lacI-lacZ fusion protein

*Escherichia coli* XAc/Δ14(33), containing the lacI and lacZ gene fusion encodes a fusion protein with both LacI repressor and β-galactosidase activity. The *E. coli* strain was grown overnight in baffled Erlenmeyerflasks containing Tryptic Soy Broth (30 g/l), (Difco, U.S.A.), with addition of Yeast Extract (7 g/l) at 37° C. overnight. Cell extracts were obtained by sonication (34) in a TST buffer (0.1M Tris-HCl, pH=7.5, 0.15M NaCl, 0.1% Tween) with addition of 0.1% BSA, 0.1 mM $ZnCl_2$, 1.0 mM$MgCl_2$ and 10 mM β-mercaptoethanol. The fusion protein was purified by $(NH_4)_2SO_4$ precipitation, using the fraction between 25 and 45% $(NH_4)_2SO_4$ saturation, followed by affinity binding to Heparin-Sepharose column (Pharmacia, Sweden). The fusion-protein was eluted in a 0.25M KCl and 15% glycerol buffer.

(d) Colorimetric DIANA of chlamydia in clinical samples

Several clinical samples of human urogenital origin was used to investigate the DIANA concept as outlined in FIG. 18. A standard cell culture assay (35) was carried out in parallel on the same samples. The *C. trachomatis* serovar L2 cell culture (FIG. 21) was used as a positive control in the assay.

The 9 samples were amplified as described in Example 5(b) and the obtained material was immobilised to Dynabeads M280-streptavidin.

The recombinant fusion protein consisting of the lac repressor enzyme conjugate (Example 5(c)) was added.

The beads, with the immobilized DNA, were mixed together with 200 μl of desalted fusion protein (LacI-lacZ, OD=0.2) and 200 μg of sonicated herring sperm DNA in a Eppendorf tube for 30 minutes. The beads was washed with the TST-buffer. The substrate, orthonitrophenyl-β-D-galactoside (ONPG), was added and the change of absorbence at room temperature was analyzed. One unit is defined as the change of one A unit per minute at 405 nm.

The results shown in FIG. 21 demonstrates a good correlation between the DIANA assay and the conventional cell culture assay. The absorbences for the negative samples are very low and confirms the low background levels obtained after a two step PCR.

(e) Solid phase DNA sequencing of positive samples

The positive samples obtained by the DIANA assay (FIG. 21) were all directly sequenced using the solid phase procedure outlined in FIG. 18. One strand of the bound DNA fragment and the enzyme conjugate were eluted simultaneously with alkali and the remaining immobilized strand was used as template for genomic sequencing. A fluorescent primer corresponding to the lac operator sequence was used.

The DNA was sequenced by melting the strands with 0.15M NaOH at room temperature in 10 minutes. The beads were thereafter washed three times with 50 μl TE buffer (0.1M Tris-HCl, pH=7.5, 1 mM EDTA). For the annealing of primer a buffer containing: 10 mM Tris-HCl, pH=7.5, 100 mM NaCl, 10 mM $MgCl_2$ and 0.1 mg/ml BSA was mixed together with 2 pmole RIT43 primer in a total volume of 17 μl. The annealing mixture was heated at 65° C. and allowed to cool to room temperature. To the mixture was thereafter 1 μl of MID solution (Pharmacia, Sweden) and 3 units of T7 DNA polymerase (Pharmacia, Sweden) added to total volume of 20 μl. To 2.5 μl of Pharmacia's nucleotide mixtures (A, C, G and T) was 4.5 μl of the solution above mixed and incubated in 10 minutes at 37° C. The beads were washed with H$_2$O and incubated at 85° C. with 3 μl of deionized fromamide to denaturate the strands. 4 μl of the generated single strand were loaded on a 7% polyacrylamide gel on the A.L.F. sequencing apparatus (Pharmacia LKB AB, Sweden).

A clear sequence was obtained for all positive samples and the results for one of the samples (number 1 in FIG. 21) is shown in FIG. 22 and SEQ ID NO:21.

REFERENCES

1. Boyer, H. W. & Roulland-Dussoix, D. (1969) *J. Mol. Biol.* 41, 459–472
2. Messing, J., Crea, R. & Seeburg, P. H. (1981) *Nucleic Acids Res.*, 309–321
3. Yamsura, D. G. and Henner, D., personal communication
4. Dente, L., Cesareni, G. & Cortese, R. (1983) *Nucleic Acids Res.* 11, 1645–1655
5. Certa, U., Vannwarth, W., Stuber, D., Gentz, R., Lanzer, M., Le Grice, S., Guillot, F., Wendler, I., Hunsmann, G., Boujard, H. & Mous, J. (1986) *EMBO J.* 5, 3051–3056
6. Birjer Jansson, Master Graduate Thesis, Royal Institute of Technology, Stockholm, Sweden 1985.
7. Nygren, P.-A., Eliasson, M., Palmcrantz, E., Abrahmse'n, L., & Uhlen, M. (1988) *J. Molecular Recognition* 1
8. Casaban, M. J., Martinez-Arias, A., Shapira, S. K. & Chou, J. (1983) *Methods Enzymol.* 100, 293–308 Vieira, J. & Mesing, J. (1987) *Methods Enzymolo.* 153, 3–11
10. Iordanescu, S. (1975), *J. Bacteriol.* 12, 597–601
11. Obtained from National Veterinary Institute, Uppsala, Sweden
12. Uhlen, M., Flock, J.-I., Philipson, L. (1981) *Plasmid* 5, 161–169.
13. Zolg W., Scott E. and Wendlinger M. (1988) Am. J. Trp. Med. Hyg. 39(1) 33–40
14. Holmberg, M. Vaidya, A. B., Shenton, F. C., Snow, R. W., Greenwood B. M., Wigzell, H. and Pettersson U. (1989) Trans. R. Soc. Trop. Med. Hyg., 84, in press
15. Updyke, T. V. and Nicholson, G. L. (1986) *Methods in Enz.* 121 717–725
16. Maniatis, T., Fritsch, E. F. & Sambrook, J. (1982) *Molecular cloning*, Cold Spring Harbour Laboratory,
17. Carter, P., *Methods Enzymol.* 154, 382–4030
18. Uhlen, M., Nilsson B., Guss, B., Lindberg, M., Gatenbeck, S. & Philipson, L. (1983) *Gene* 23, 369–685
19. Laemmli, U. K., *Nature* 227, 680–685
20. Clark I. N., Ward M. E. and Lambden P. R. (1988) Gene 71, 307–314
21. Favalor, J. M., Coppel R. L., Corcran, L. M., Foote, S. J., Brown, G. V., Anders, R. F. & Kemp, D. J. (1986) Nucl. Acid. Res 14, 8265–8278
22. Perlmann, H., Berzins, K., Wahlgren, M., Carlsson, J., Björkman, A., Patarroyo M. E. and Perlmann, P. (1984) J. Exp. Med., 159, 1686–1704
23. Coppel, R. L., Cowman, A. F., Anders R. F., Bianco, A. E., Saint, R. B., Lingelbach, K. R., Kemp D. J. and Brown G. V. (1984) Nature, 310, 789–792
24. Hultman T, Ståhl S., Hornes E. and Uhlén M. (1989) Nucl. Acids. Res. 17, 4937–4946
25. Wang S.-P. and Graystone J. T. (Nichols, R. L.) (pp. 305–321). Excerpta Medca, Amsterdam, 1971
26. Wang S.-P., Kuo C.-C., Barnes R. C., Stephens R. S. and Graystone J. T. (1985) J. Infect. Dis.152, 791–800
27. Schachter J. and Caldwell H. D. (1980) Chlamydiae. Annu. Rev. Microbiol. 34, 285–309
28. Pickett M. A., Ward M. E. and Clark I. N. (1987) FEMS Microbiology Letters 42 185–190
29. Stephens R. S., Sanchez-Pescador R., Wagar E. A., Inouye C. and Urdea M. S. (1987) J. Bacteriol. 169 3879–3885
30. Bavoil P., Ohlin A. and Schachter J. (1984) Infect. Immun. 44, 4790–485
31. Barbour A. G., Amano K.-I., Hackstadt T., Perry L. and Caldwell H. D.(1982) J. Bacteriol. 151, 420–428
32. Lea T., Vartdal F., Nustad K., Funderud S., Berge A., Ellingsen T., Schmid R., Stenstad P. and Ugelstad J. (1988) J. of Mol. Recogn. 1, 9–18
33. Coulondre C. and Miller J. H. (1977) J. Mol. Biot 117, 59–71 Dean et al
34. Uhlén, M., Nilsson, B., Guss, B., Lindberg, M., Gatenbeck, S. & Philipson, L. (1983) Gene 23, 369–378
35. Evans R. T. and Woodland R. M. (1983) British Medical Bulletin 39, 181–186

---

I claim:

1. A method for detecting a target polynucleotide that is characteristic of a pathological condition, comprising the steps of:
   (a) producing a first amplified DNA by a first polymerass chain reaction using a first set of primers to amplify a target polynucleotide characteristic of a pathological condition;
   (b) producing from said first amplified DNA a second amplified DNA by a second polymerass chain reaction using a second set of primers, wherein:
   (i) said second primers differ from said first primers,
   (ii) a 5' region of said second primers is not complementary to said first amplified DNA,
   (iii) one of said second primers is biotinylated, and
   (iv) another of said second primers comprises means for binding a detectable label;
   (c) binding said biotinylated second primer to a solid support before, during or after said second polymerase chain reaction, whereby said second amplified DNA is bound to said support;
   (d) binding a detectable label to said means for binding a detectable label after said second polymerase chain reaction, whereby said detectable label is bound to said second amplified DNA, wherein said second amplified DNA is double-stranded; and
   (e) detecting said target polynucleotide by determining the detectable label bound to said double-stranded second amplified DNA.

2. A kit for detecting a target polynucleotide that is characteristic of a pathological condition, said target polynucleotide being first amplified by a first polymerase chain reaction using first primers, said kit comprising a set of second primers for producing a second amplified DNA from said first amplified DNA, wherein:
   (i) said second primers differ from said first primers,
   (ii) a 5' region of said second primers is not complementary to said first amplified DNA,
   (iii) one of said second primers is biotinylated, and
   (iv) another of said second primers comprises means for binding a detectable label,
   said biotinylated second primer being effective, before, during or after said second amplification reaction, to immobilize said second amplified DNA on a solid support comprising a biotin-binding moiety, and
   said means for binding a detectable label being effective, after said amplification reaction, to bind a label to said second amplified DNA, wherein said second amplified DNA is double-stranded, whereby said target polynucleotide may be detected by determining said label bound to said double-stranded second amplified DNA.

3. A method for detecting a target polynucleotide that is characteristic of a pathological condition, comprising the steps of:
   (a) producing a first amplified DNA by a first polymerase chain reaction using a first set of primers to amplify in a diagnostic sample a target polynucleotide characteristic of a pathological condition;
   (b) producing from said first amplified DNA a second amplified DNA by a second polymerase chain reaction using a second set of primers, wherein (i) said second primers differ from said first primers, and (ii) a 5' region of said second primers is not complementary to said first amplified DNA, (c) producing a third amplified DNA from said second amplified DNA by a third polymerase chain reaction using a third set of primers, wherein (i) the 3' region of said third primers hybridizes to said second amplified DNA in said 5' regions that are not complementary to said first amplified DNA, (ii) one of said third primers is biotinylated for binding a solid support, and (iii) another of said third primers comprises means for binding a detectable label;

(d) binding said third amplified DNA to a solid support via said biotinylated third primer, before, during or after said third polymerase chain reaction;

(e) binding a detectable label to said third amplified DNA via said means for binding a detectable label after said third polymerase chain reaction, wherein said third amplified DNA is double-stranded; and (f) detecting said target polynucleotide by determining the detectable label bound to said double-stranded third amplified DNA.

4. A method as claimed in claim 1 in which said solid support comprises magnetic particles.

5. A method as claimed in claim 4 in which the solid support comprises monodisperse, superparamagnetic particles.

6. A method as claimed in claim 1 in which said solid support is selected from the group consisting of a microtitre well, a dipstick, non-magnetic particles, fibres and capillaries.

7. A method as claimed in claim 1 in which after said second amplified DNA is immobilised on said solid support, said second amplified DNA is subjected to strand separation, and the resulting single-stranded DNA immoblised on said solid support is sequenced.

8. A method as claimed in claim 7 wherein said means for binding a detectable label is the lac operon, said detectable label is a lacI protein fused to an enzyme capable of generating a detectable signal, and wherein said method further comprises the steps of:

(f) subjecting said second amplified DNA to strand separation whereby lablelled, single-stranded DNA is released from said solid support and biotinylated, single-stranded DNA remains immobilized on said solid support, and (g) subjecting said biotinylated, single-stranded DNA to sequencing wherein said steps (f) and (g) occur after said step (e) of detecting said target polynucleotide by determining the detectable label that binds to said second amplified DNA.

9. A method according to claim 1 wherein said means for binding a detectable label is a sequenc-specific binding site for a sequence-specific DNA binding protein.

10. A kit according to claim 2, wherein said means for binding a detectable label is a sequence-specific binding site for a sequence-specific DNA binding protein.

11. A kit according to claim 10, wherein said sequence-specfic binding site is a binding site for a lacI protein.

12. A kit according to claim 2, further comprising a solid support wherein said solid support is selected from the group consisting of a microtitre well, a dipstick, non-magnetic paraticles, fibres and capillaries.

13. A kit according to claim 2, further comprising a solid support, wherein said solid support is a superparamagnetic, monodisperse magnetic bead.

14. A method according to claim 3, wherein said means for binding a detectable label is a sequence-specific binding site for a sequence-specific DNA binding protein.

15. A method according to claim 14, wherein said sequence-specific binding site for binding a detectable label is a sequence-specific binding site for a lacI protein.

16. A method according to claim 3, wherein said solid support is a superparamagnetic, monodisperse magnetic bead.

17. A method as claimed in claim 9, wherein said sequence-specific binding site is a binding site for a lacI protein.

18. A method as claimed in claim 17, wherein said sequence specific DNA binding protein is a lacI protein and said sequence-specific binding site is the lac operon.

19. A method as claimed in claim 7 in which said lacI protein is fused to an enzyme label.

20. A kit according to claim 2, further comprising a solid support comprising a biotin-binding moiety.

21. A kit according to claim 20, further comprising a detectable label.

* * * * *